(12) United States Patent
Robinson et al.

(10) Patent No.: US 12,064,354 B2
(45) Date of Patent: Aug. 20, 2024

(54) COMPOSITE POROUS INTERBODIES AND METHODS OF MANUFACTURE

(71) Applicant: Alphatec Spine, Inc., Carlsbad, CA (US)

(72) Inventors: Scott Robinson, Carlsbad, CA (US); Steven Leong, Carlsbad, CA (US); Frank Chang, Carlsbad, CA (US)

(73) Assignee: ALPHATEC SPINE, INC., Carlsbad, CA (US)

( * ) Notice: Subject to any disclaimer, the term of this patent is extended or adjusted under 35 U.S.C. 154(b) by 113 days.

(21) Appl. No.: 17/482,829

(22) Filed: Sep. 23, 2021

(65) Prior Publication Data
US 2022/0087819 A1 Mar. 24, 2022

Related U.S. Application Data

(60) Provisional application No. 63/082,782, filed on Sep. 24, 2020.

(51) Int. Cl.
*A61F 2/44* (2006.01)
*A61F 2/30* (2006.01)
(Continued)

(52) U.S. Cl.
CPC ........ *A61F 2/4455* (2013.01); *A61F 2/30749* (2013.01); *A61F 2/3094* (2013.01);
(Continued)

(58) Field of Classification Search
CPC ........ A61F 2/3094; A61F 2/44; A61F 2/4455; A61F 2/447; A61F 2002/30967; A61F 2002/30971
See application file for complete search history.

(56) References Cited

U.S. PATENT DOCUMENTS 5,275,601 A 1/1994 Gogolewski et al.
5,496,372 A 3/1996 Hamamoto et al.
(Continued)

FOREIGN PATENT DOCUMENTS

EP 1477190 A1 11/2004
GB 2500514 B 7/2015
(Continued)

OTHER PUBLICATIONS

European Patent Office acting as International Searching Authority, "Search Report and Written Opinion," International Application No. PCT/US2021/051679, Feb. 28, 2022.
(Continued)

*Primary Examiner* — Eric S Gibson
(74) *Attorney, Agent, or Firm* — Dentons Durham Jones Pinegar; Sarah W. Matthews

(57) ABSTRACT

A method of forming a composite titanium body for use in forming spinal implant interbodies includes selecting a metal alloy body, carving out a top portion and a bottom portion from the metal alloy body, and bonding a porous material to the carved-out top and bottom portions. Multiple pieces may be cut from the composite titanium body, each having a front face formed of the metal alloy, top and bottom portions formed of the porous material, and with a medial portion of the metal alloy extending from the front face to the back. Methods and devices for spinal interbodies having locking mechanisms to prevent bone screw back-out are also described.

8 Claims, 18 Drawing Sheets

(51) Int. Cl.
 *B23K 20/02* (2006.01)
 *B23K 103/14* (2006.01)
(52) U.S. Cl.
 CPC .............. *A61F 2002/30011* (2013.01); *A61F 2002/30405* (2013.01); *A61F 2002/30517* (2013.01); *A61F 2002/30784* (2013.01); *A61F 2002/30967* (2013.01); *A61F 2310/00023* (2013.01); *B23K 20/023* (2013.01); *B23K 2103/14* (2018.08)

(56) References Cited

U.S. PATENT DOCUMENTS

| | | |
|---|---|---|
| 5,732,469 A | 3/1998 | Hamamoto et al. |
| 5,888,223 A | 3/1999 | Bray, Jr. |
| 6,051,117 A | 4/2000 | Novak et al. |
| 6,066,175 A | 5/2000 | Henderson et al. |
| 6,206,922 B1 | 3/2001 | Zdeblick et al. |
| 6,579,290 B1 | 6/2003 | Hardcastle et al. |
| 7,077,864 B2 | 7/2006 | Byrd, III et al. |
| 7,208,222 B2 | 4/2007 | Rolfe et al. |
| 7,232,464 B2 | 6/2007 | Mathieu et al. |
| 7,458,991 B2 | 12/2008 | Wang et al. |
| 7,794,502 B2 | 9/2010 | Michelson |
| 7,972,363 B2 | 7/2011 | Moskowitz et al. |
| 8,303,879 B2* | 11/2012 | Bertele ............... A61F 2/30907 264/273 |
| 8,328,872 B2* | 12/2012 | Duffield ............. A61B 17/8042 623/17.16 |
| 8,377,139 B2 | 2/2013 | Laubert et al. |
| 8,414,820 B2* | 4/2013 | Bertele .................. A61F 2/447 264/453 |
| 8,419,797 B2 | 4/2013 | Biedermann et al. |
| 8,425,607 B2 | 4/2013 | Waugh et al. |
| 8,465,546 B2 | 6/2013 | Jodaitis et al. |
| 8,500,811 B2 | 8/2013 | Blain et al. |
| 8,685,100 B2 | 4/2014 | Jodaitis et al. |
| 8,728,165 B2 | 5/2014 | Parry et al. |
| 8,734,516 B2 | 5/2014 | Moskowitz et al. |
| 8,753,396 B1 | 6/2014 | Hockett |
| 8,795,373 B2* | 8/2014 | Jones ..................... A61F 2/4465 606/296 |
| 8,864,832 B2 | 10/2014 | Carls et al. |
| 8,870,961 B2 | 10/2014 | Thalgott et al. |
| 8,882,843 B2 | 11/2014 | Michelson |
| 8,932,366 B2* | 1/2015 | Shih .......................... A61F 2/28 623/23.57 |
| 9,017,412 B2 | 4/2015 | Wolters et al. |
| 9,066,815 B2 | 6/2015 | Garber et al. |
| 9,089,431 B2 | 7/2015 | Grohowski, Jr. |
| 9,168,147 B2 | 10/2015 | Patterson et al. |
| 9,277,946 B2* | 3/2016 | Hooper .............. A61B 17/8047 |
| 9,308,076 B2 | 4/2016 | Ringeisen et al. |
| 9,486,325 B2 | 11/2016 | Davenport et al. |
| 9,622,875 B2 | 4/2017 | Moskowitz et al. |
| 9,707,320 B2 | 7/2017 | Daigo et al. |
| 9,707,321 B2* | 7/2017 | Daigo ..................... A61L 27/06 |
| 9,724,203 B2* | 8/2017 | Nebosky ................. A61F 2/442 |
| 9,744,052 B2 | 8/2017 | Moskowitz et al. |
| 9,918,750 B2 | 3/2018 | Tipping et al. |
| 9,968,461 B2* | 5/2018 | Zappacosta ........... A61F 2/4455 |
| 10,117,746 B2 | 11/2018 | Cordaro |
| 10,159,582 B2 | 12/2018 | Gamache |
| 10,327,910 B2* | 6/2019 | Kirschman ........... A61F 2/4455 |
| 10,376,379 B2 | 8/2019 | Songer |
| 10,413,426 B2 | 9/2019 | Parry et al. |
| 10,512,547 B2* | 12/2019 | Altarac ................ A61F 2/4455 |
| 10,575,960 B2 | 3/2020 | Duffield et al. |
| 10,792,129 B2 | 10/2020 | Spivack et al. |
| 10,898,333 B2 | 1/2021 | Cordaro |
| 10,952,870 B2 | 3/2021 | Scott-Young |
| 10,980,641 B2* | 4/2021 | Altarac .............. A61B 17/8042 |
| 11,000,321 B2* | 5/2021 | White ................ A61F 2/30771 |
| 11,058,552 B2 | 7/2021 | Zink et al. |
| 11,173,042 B2* | 11/2021 | Walsh .................. A61F 2/4455 |
| 2003/0220696 A1 | 11/2003 | Levine et al. |
| 2005/0100578 A1 | 5/2005 | Schmid et al. |
| 2008/0177307 A1* | 7/2008 | Moskowitz ........ A61B 17/7074 606/301 |
| 2009/0105830 A1* | 4/2009 | Jones ................ A61B 17/8042 606/301 |
| 2010/0057206 A1* | 3/2010 | Duffield ..................... A61F 2/44 606/279 |
| 2010/0312346 A1* | 12/2010 | Kueenzi .................... A61F 2/44 623/17.16 |
| 2011/0190888 A1* | 8/2011 | Bertele .................... A61F 2/447 623/17.11 |
| 2012/0167367 A1* | 7/2012 | Bertele ............... A61F 2/30734 29/446 |
| 2012/0172991 A1* | 7/2012 | Bertele .................... A61F 2/447 623/17.16 |
| 2012/0232599 A1* | 9/2012 | Schoenly ............. A61B 17/863 606/104 |
| 2012/0239154 A1 | 9/2012 | Ullrich, Jr. et al. |
| 2013/0060336 A1* | 3/2013 | Hooper .................... A61F 2/447 623/17.11 |
| 2013/0180970 A1* | 7/2013 | Vargas ................. B23K 9/0008 219/136 |
| 2013/0226309 A1* | 8/2013 | Daigo ..................... A61L 27/56 623/23.55 |
| 2013/0230738 A1* | 9/2013 | Daigo ..................... A61L 27/56 428/613 |
| 2014/0052255 A1* | 2/2014 | DeFalco ............. A61B 17/8057 606/286 |
| 2014/0277456 A1* | 9/2014 | Kirschman ............. A61F 2/447 623/17.11 |
| 2014/0277461 A1* | 9/2014 | Nebosky .................. A61F 2/442 156/60 |
| 2015/0018956 A1* | 1/2015 | Steinmann ................ A61F 2/34 419/53 |
| 2015/0328007 A1* | 11/2015 | Padovani ................ A61F 2/442 623/17.13 |
| 2015/0328009 A1* | 11/2015 | Zappacosta ............ A61F 2/442 623/17.16 |
| 2016/0151166 A1 | 6/2016 | Morris et al. |
| 2017/0056190 A1 | 3/2017 | Guilford et al. |
| 2017/0156869 A1* | 6/2017 | Uzuyem ..................... A61F 2/32 |
| 2017/0156880 A1 | 6/2017 | Halverson et al. |
| 2017/0246011 A1 | 8/2017 | Matsumoto et al. |
| 2018/0110624 A1 | 4/2018 | Arnone |
| 2018/0318099 A1* | 11/2018 | Altarac .............. A61B 17/8042 |
| 2018/0318100 A1* | 11/2018 | Altarac ................ A61F 2/4455 |
| 2019/0343644 A1 | 11/2019 | Ryan et al. |
| 2020/0197189 A1 | 6/2020 | Mazur et al. |
| 2021/0059834 A1* | 3/2021 | Miguel ............... A61F 2/30749 |
| 2021/0154022 A1* | 5/2021 | Walsh ..................... A61F 2/447 |
| 2021/0251769 A1* | 8/2021 | Hapstack .............. A61F 2/4455 |
| 2022/0087819 A1* | 3/2022 | Robinson ................ A61L 27/56 |

FOREIGN PATENT DOCUMENTS

| | | | | |
|---|---|---|---|---|
| WO | 2009064644 A1 | 5/2009 | | |
| WO | 2010054181 A1 | 5/2010 | | |
| WO | WO-2011094748 A1 * | 8/2011 | ......... | A61F 2/30734 |
| WO | WO-2012121726 A1 * | 9/2012 | ........... | A61B 17/863 |
| WO | WO-2014143719 A1 * | 9/2014 | ............... | A61F 2/44 |
| WO | 2016148923 A1 | 9/2016 | | |

OTHER PUBLICATIONS

International Preliminary Report on Patentability, International Application No. PCT/US2021/051679, Apr. 6, 2023.

\* cited by examiner

COMPOSITE POROUS INTERBODIES AND METHODS OF MANUFACTURE

RELATED APPLICATIONS

The present application claims priority to U.S. Provisional Application No. 63/082,782, filed Sep. 24, 2020, the entire contents of which are incorporated herein by reference.

TECHNICAL FIELD

The present disclosure relates generally to implants for the spine. More specifically, and without limitation, the present disclosure relates to spinal interbody implants and methods of manufacturing spinal interbody implants.

RELATED ART

Spinal surgery may be used to treat various conditions, such as degenerative disc disease, recurrent disc herniation, spinal instability, spondylolisthesis, pseudo arthrosis, osteomyelitis/discitis, post-laminectomy syndrome and trauma. Spinal fusion treatment is typically used for intractable lower back pain arising from degenerative disc disease and/or spinal instability. Fusion includes immobilizing the painful spine segments and encouraging bone growth across the immobilized level. In the cervical spine, anterior decompression and fusion is typically used.

Spinal fusion implants are often designed to facilitate bone in-growth because the clinical outcome of lumbar spinal fusion is correlated with achievement of bony fusion. Achieving bone integration with an interbody implant is likely to aid fusion and improve implant longevity by limiting subsidence and stress shielding and associated complications. Indeed, improving interbody implant bone on-growth and in-growth may enhance fusion, limiting pseudoarthrosis, stress shielding, subsidence and implant failure.

Titanium and its alloys are often selected for interbody construction because titanium has good biocompatibility, robust repassivation that is attributable to $TiO_2$ formation which provides good resistance to corrosion, and low density. Although titanium alloys have desirable biocompatibility and mechanical properties, further modification is often needed to support osseointegration. For example, modifications may include a rough surface, modified surface topography, heat treatment, alkali treatment, removal of Na ions, porous material conversion, and/or HA coating. These modifications can improve its osseointegrative potential and bioactivity. Porous titanium can be helpful for osseointegration, but also has limitations. For example, porous titanium is not as strong or as durable as solid titanium.

Another issue with spinal implants is that they may use bone anchors to fix the interbody in place between adjacent vertebrae. Over time, due to micro motion of the vertebrae relative to the implant, the bone anchors may loosen and start to back-out of vertebrae. In addition to possibly allowing the implant to become loose and potentially displace within the vertebral space, the bone anchors themselves may protrude and cause damage to sensitive tissue and organs in the patient.

There is a need for improved implant designs which will further enhance both the short and long term stability of the implant and promote fusion.

SUMMARY

According to one aspect, a method is disclosed for manufacturing a composite interbody, the method comprising: selecting a metal alloy body having a top surface and an opposing bottom surface; carving or boring out a portion of the top surface of the metal alloy body; carving or boring out a portion of the bottom surface of the metal alloy body; bonding porous metal to the top surface; bonding porous metal to the bottom surface to form a composite metal alloy block; and cutting out a composite interbody from the composite metal alloy block. In some configurations, the metal alloy comprises a titanium alloy and the porous metal comprises porous titanium. According to another aspect, fusion bonding may be used to fuse the porous material to the metal alloy body.

Also disclosed herein are composite interbodies, such as interbodies formed of the composite metal alloy block formed as described in the methods herein. For example, an ALIF composite interbody system may include: a body having an anterior face and an opposing posterior face, a top portion and a bottom portion, with a medial portion extending through the body from the anterior face to the opposing posterior face; the anterior face formed of titanium alloy, the top portion and bottom portion formed of porous titanium, and the medial portion formed of titanium alloy. In some configurations, the anterior face and medial portion are formed of a single piece of titanium alloy.

According to yet another aspect, a locking mechanism is described to prevent back-out of bone anchors from composite interbodies. A composite interbody system may include: a body having an anterior face and an opposing posterior face, a top portion and a bottom portion, with a medial portion extending through the body from the anterior face to the opposing posterior face; the anterior face formed of a solid metal alloy, the top portion and bottom portion formed of a porous metal, and the medial portion formed of a solid metal alloy; the anterior face comprising at least one bore for receiving a bone screw; and at least one locking mechanism for preventing back-out of the bone screw.

A locking mechanism may include an axial channel proximal to a bore, wherein the locking mechanism comprises a cylinder with an outwardly projecting tab, the cylinder receivable in the axial channel, and the outwardly projecting tab extending into the at least one bore. In some configurations the outwardly projecting tab of the locking mechanism further comprises an angled face to allow the bone screw to deflect the outwardly projecting tab as it is inserted into the at least one bore. The outwardly project tab may be biased to extend into the at least one bore after it is deflected by the bone screw.

In some configurations, a composite interbody system may comprise an anterior face comprising a first bore for receiving a first bone screw, and a first inwardly extending channel proximal to the first bore, the inwardly extending channel for receiving a first locking mechanism; the anterior face comprising a second bore for receiving a second bone screw, and a second inwardly extending channel proximal to the second bore, the second inwardly extending channel for receiving a second locking mechanism; the first locking mechanism comprising a cylinder receivable into the first inwardly extending channel, the cylinder having an inward end and an outward end, and a tab projecting outwardly from the outward end of the cylinder, the tab projecting at least partially into the first bore; and the second locking mechanism comprising a cylinder receivable in the second inwardly extending channel, and a tab projecting outwardly from the cylinder, the tab projecting at least partially into the second bore.

According to another aspect, the outward end of the cylinder of the locking mechanism comprises a cut-away to allow the tab of the first locking mechanism to be forced out of the first bore by pressure of an inwardly moving first bone anchor and the tab of the second locking mechanism to be forced out of the second bore by pressure of an inwardly moving second bone anchor. Each of the tabs of the first and second locking mechanism are biased toward projecting at least partially into the first bore and the second bore, respectively.

According to another aspect, a cervical composite interbody is described, and may include: a body having an anterior face and an opposing posterior face, a top portion and a bottom portion, with a medial portion extending through the body from the anterior face to the opposing posterior face, the medial portion separating the top portion and the bottom portion; the anterior face formed of a solid metal alloy, the top portion and bottom portion formed of a porous metal, and the medial portion formed of a solid metal alloy; the anterior face comprising a first bore for receiving a first bone anchor; the anterior face comprising a second bore for receiving a second bone anchor; and a locking mechanism to prevent back-out of the first bone anchor and the second bone anchor from the first and second bores, respectively.

According to another aspect, the anterior face of the cervical implant includes a shaped void for receiving the locking mechanism, the shaped void between the first bore and the second bore; and the locking mechanism comprises a rotatable blocker positioned in the shaped void between the first bore and the second bore, the rotatable blocker having a first, open position wherein bone anchors may be inserted and a second, closed position wherein bone anchors may not be inserted. In some configurations the shaped void may also include additional cut-outs for receiving/mating with an insertion tool.

In some configurations, the body of the cervical implant comprises a vertical opening, the locking mechanism further comprises a vertical pin, and the rotatable blocker comprises an aperture for receiving the vertical pin to hold the rotatable blocker in place in the body. The rotatable blocker may have a first outwardly extending arm and a second outwardly extending arm, and wherein the shaped void comprises a first slot for the first outwardly extending arm to rotate within and a second slot for the second outwardly extending arm to rotate within.

According to another aspect, the implants described herein may be cut/formed from a composite metal block that is formed using the methods described herein. The implants cut/formed from a composite metal block formed by the methods described herein will have a solid metal anterior face, with a solid metal medial portion extending from the anterior face to the posterior face, and upper and lower portions formed of porous material. The upper and lower portions may be diffusion bonded to the medial portion.

Other aspects of the disclosed subject matter, as well as features and advantages of various aspects of the disclosed subject matter, should be apparent to those of ordinary skill in the art through consideration of the ensuing description, the accompanying drawings, and the appended claims.

BRIEF DESCRIPTION OF DRAWINGS

The following drawings illustrate what are currently considered to be specific representative configurations for carrying out the disclosed subject matter and are not limiting as to embodiments which may be made in accordance with this disclosure. The components in the drawings are not necessarily to scale relative to each other. Like reference numerals designate corresponding parts throughout the several views.

DETAILED DESCRIPTION

Hereinafter, exemplary embodiments of the present disclosure will be described in detail with reference to the accompanying drawings. Advantages and features of the present disclosure and methods accomplishing them will become apparent from the following description of exemplary embodiments with reference to the accompanying drawings. Various aspects discussed in reference to one drawing may be present and/or used in conjunction with the embodiment shown in another drawing, and each element shown in multiple drawings may be discussed only once.

Reference in the specification to "one configuration," "one embodiment," "a configuration," or "an embodiment" means that a particular feature, structure, or characteristic described in connection with the configuration is included in at least one configuration, but it is not a requirement that such feature, structure, or characteristic be present in any particular configuration unless expressly set forth in the claims as being present. The appearances of the phrase "in one configuration" in various places may not necessarily limit the inclusion of a particular element of the invention to a single configuration, rather the element may be included in other or all configurations discussed herein.

The described features, structures, or characteristics of configurations of the disclosed subject matter may be combined in any suitable manner in one or more configurations. As used in this specification and the appended claims, singular forms such as "a," "an," and "the" may include the plural unless the context clearly dictates otherwise. Thus, for example, reference to "a block" of solid titanium may include one or more of such blocks, and reference to "the bore" may include reference to one or more of such bores. Structural elements, compositional elements, and/or materials may be presented in a common list for convenience. However, these lists should be construed as though each member of the list is individually identified as a separate and unique member.

Certain components of the composite interbody described herein will be described as being coupled or connected to one another, and such connections and couplings may be achieved in any suitable manner. Additionally, such components may be integrated with one another or distributed in any suitable fashion. As used herein, a "block" of material means any body of such material of any shape or size, such as a brick, a sheet, or another body of such material, etc.

Figure 1:
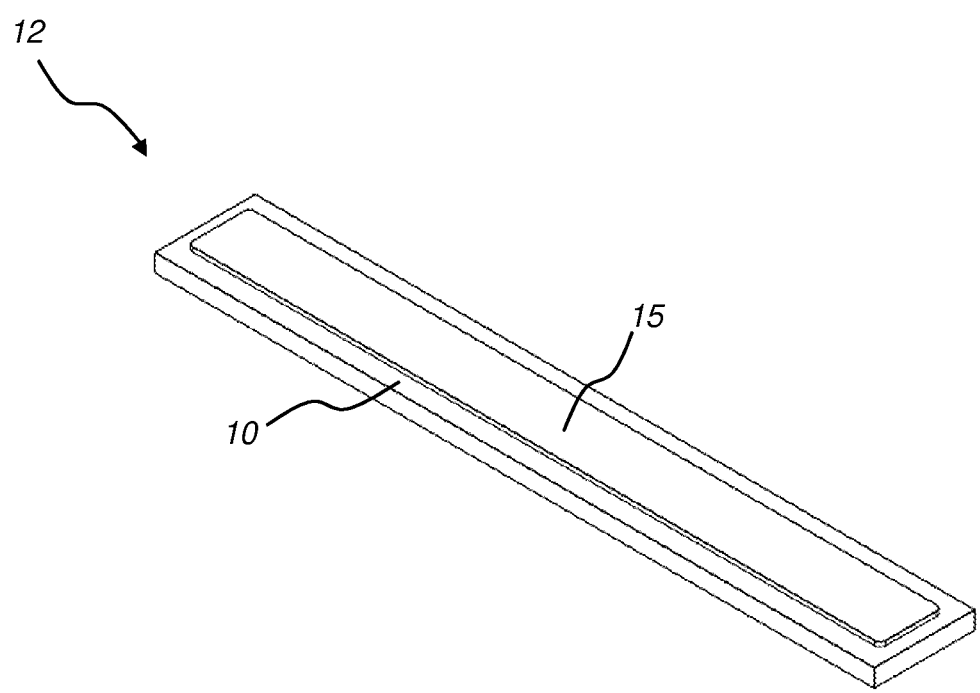
FIG. 1 is a perspective view of an example of a composite titanium body used to manufacture spinal interbodies.

This disclosure generally relates to methods of manufacturing composite interbodies. The composite interbodies may be formed of a first portion that includes a metal alloy which may be entirely or substantially non-porous, and a second portion that includes a porous material. In some configurations, the composite interbodies are formed from a brick or other body of composite material that includes a metal alloy brick or body 10 that has had a portion of its top and bottom removed, with porous material 15 bonded or otherwise attached to the top and bottom portion, as seen in FIG. 1 and described in more detail below.

Any suitable metal or metal alloy may be used for the metal alloy body 10 of the composite interbody, including, but not limited to, stainless steel, cobalt-chromium, titanium (Ti), titanium alloys, shape memory alloys, e.g., NiTi, tantalum (Ta), niobium (Nb), zirconium (Zr) and platinum (Pt). Spinal interbodies are typically formed of metals and metal alloys including titanium, tantalum, titanium alloys, and cobalt-chromium and alloys thereof. Exemplary cobalt-chromium materials include CoCrMo alloys. Exemplary titanium alloys for use according to the present disclosure include Ti6Al4V. Exemplary stainless steel materials for use according to the present disclosure include austenitic stainless steels, especially types 316 and 316L, and Ni-free stainless steel. Titanium is a transition metal that is corrosion resistant, offers high stiffness and is physiologically inert, thereby enhancing its usefulness in a spinal implant interbody. Titanium also has the unusual ability to osseointegrate. Furthermore, the anatomical position of interbodies fabricated from titanium may be easily analyzed by conventional imaging methods.

The porous material 15 may be any suitable porous metal or metal alloy. For example, porous metal or metal alloys could be selected from, but are not limited to, stainless steel, cobalt-chromium, titanium (Ti), titanium alloys, shape memory alloys, e.g., NiTi, tantalum (Ta), niobium (Nb), zirconium (Zr) and platinum (Pt). Typical metals and metal alloys may include titanium, tantalum, titanium alloys, and cobalt-chromium and alloys thereof. The porous material may be made by any suitable method and in some configurations, it may be made by bonding thin sheets of metal or metal alloy together, where the sheets have been made porous using photolithography to achieve a uniform pore pattern in each sheet. The porous sheets may be bonded together using a method such as diffusion bonding. Other methods may also be used, and the porous structure of the porous material 15 may have a randomized pattern of open pores or a repeating pattern of open pores. The porous material 15 may feature interconnected pores or open pores.

The porous material 15 may have pores ranging in size, for example, from about 100 µm to about 2 mm, about 100µ to about 1 mm, about 200 µm to about 900 µm, or about approximately 300 µm to about 800 µm in diameter. The pore size may have an average pore size of about 300 µm to about 800 µm, about 400 µm to about 700 µm, or about 500 µm to about 600 µm. The pore size distribution may be unimodal or bi-modal. Any suitable pore shape and configuration may be used, such as spherical or partially-spherical pores, repeating or random patterns of cylinders, cubes, cones, pyramids, polyhedrons, etc. The porous material 15 may also have a suitable porosity for promoting osseointegration. For example, the porous material may be from about 30% open to about 80% open. In some configurations, the porous material may be greater than 50% open, greater than 60% open, greater than 70% open, or greater than 75% open.

Figure 2:
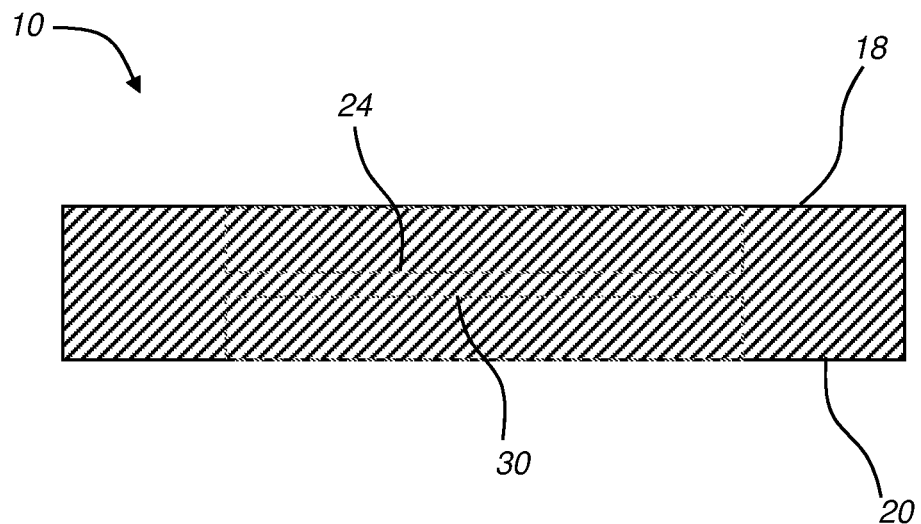
FIG. 2 is a cross-sectional view of a titanium alloy body.

The porous material 15 may be attached to the non-porous metal alloy body 10 in any suitable manner. In one configuration, the body 10 of metal alloy may first have one or more portions removed, such as by carving or boring out portions of the body 10 of the metal alloy. FIG. 2 shows a cross-sectional view of a body 10 of metal or metal alloy, which has a rectangular cross-section. This configuration uses a body 10 which is substantially shaped as a brick, but other shapes and sizes may be used for the body 10. The body may have a top surface 18 and an opposing bottom surface 20.

Figure 3:
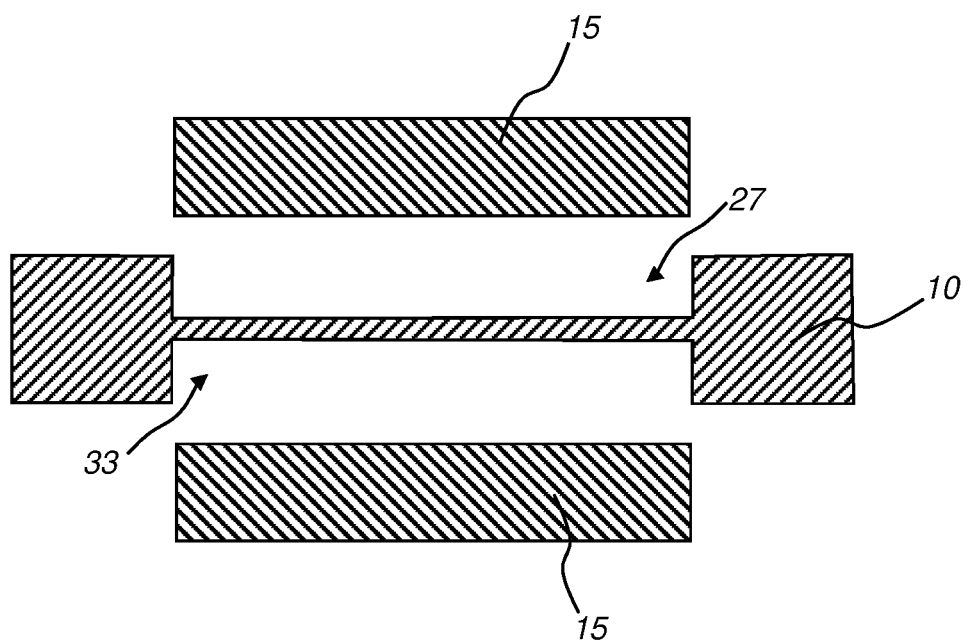
FIG. 3 is a cross-sectional, exploded view of a carved-out titanium alloy body and an upper and lower porous material.

As indicated by dashed lines 24, a portion of the top surface 18 of the body 10 may be carved or bored out or otherwise removed, forming a top portion void 27 (see FIG. 3). Similarly, as indicated by dashed lines 30 in FIG. 2, a portion of the bottom surface 20 of the body 10 may be carved or bored out or otherwise removed, forming a bottom portion void 33 (see FIG. 3). These voids can then be filled with the porous material. FIG. 3 shows an exploded cross-sectional view of the body 10 with the top portion void 27 and bottom portion void 33, as well as porous material 15 to be placed in the respective voids.

The porous material 15 may be bonded to the metal alloy body 10 in any suitable manner. By way of example and not of limitation, diffusion bonding may be used. Diffusion bonding is a solid-state bonding technique which results in an undetectable original bond line. The metal components being joined undergo only microscopic deformation, and the joining region is homogeneous without secondary materials or liquid phases. Diffusion bonding often uses an elevated temperature and high pressure to achieve a weld at the atomic level between the metal components. As the two surfaces are brought together under elevated temperature and high pressure, over time material begins to diffuse across the boundary of the abutting surfaces, blending the material boundary and creating a bond.

Figure 4:
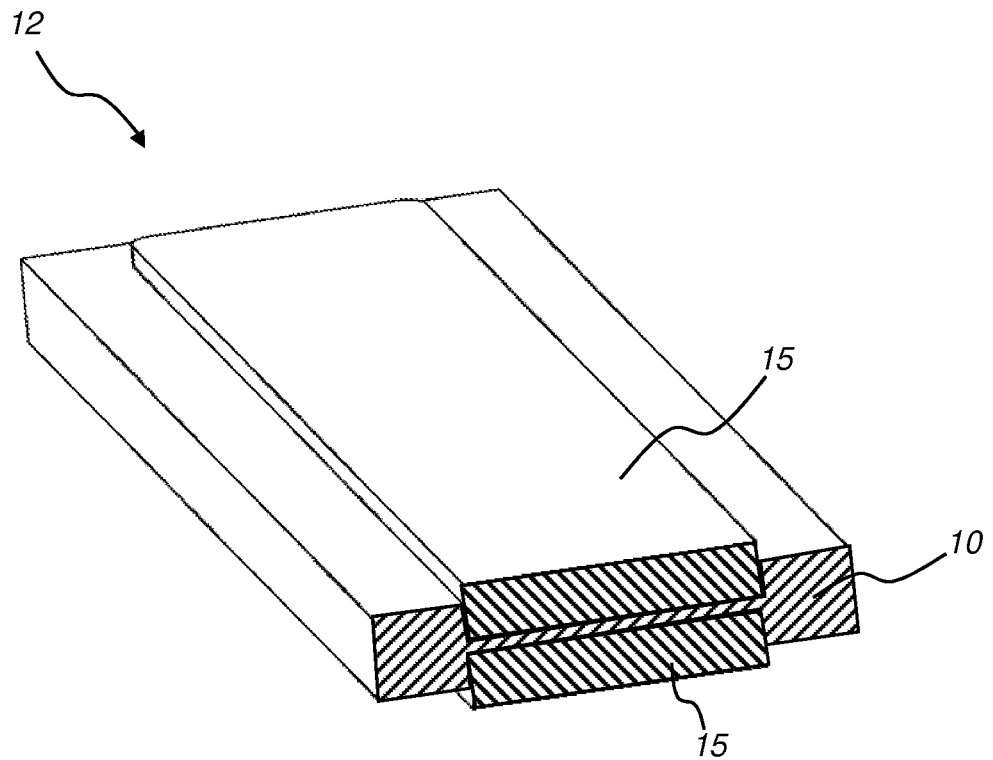
FIG. 4 is a perspective, cross-sectional view of FIG. 1.
Figure 5:
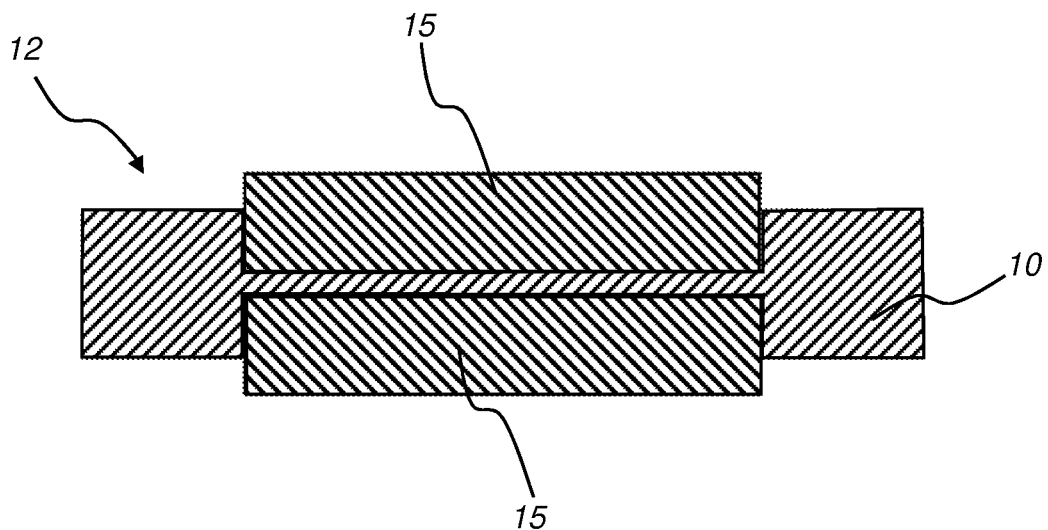
FIG. 5 is a cross-sectional front view of FIG. 1.

The composite metal alloy block 12 disclosed herein may be formed by diffusion bonding of an assembly of a first portion of metal alloy body 10 (already having a top portion and bottom portion removed), porous material 15 in the top void 27 of the metal alloy body 10, and porous material 15 in the bottom void 33 of the metal alloy body 10 (see FIGS. 4-5). These layers of porous material 15, metal alloy body 10, and porous material 15 may be diffusion bonded by placing the layers into a die and applying heat and pressure. As discussed above, diffusion bonding at an atomic level facilitates combination of surfaces that touch one another, and results in near 100% bonding.

Diffusion bonding to form the composite metal alloy block 12 may occur prior to forming the spinal interbodies from the composite metal alloy block 12. Any suitable shape and size of a composite metal alloy block 12 may be used, and any suitable shape and size may be carved out of the body 10 to form the top portion void 27. The porous material used to fill the top portion void may have a depth greater than the depth of the top portion void 27, such that it extends above the top side 18 of the metal alloy body 10. In other configurations, the porous material 15 used to fill the top portion void 27 may have a depth similar to the depth of the top portion void 27 or less than the depth of the top portion void 27.

Similarly, the bottom portion void 33 may be carved out of the body 10. The bottom portion void 33 may have any suitable shape and size. The porous material 15 used to fill the bottom portion void 33 may have a depth greater than the depth of the bottom portion void 33, such that it extends below the bottom surface 20 of the metal alloy body 10. In other configurations, the porous material 15 used to fill the bottom portion void 33 may have a depth similar to the depth of the bottom portion void 33 or less than the depth of the bottom portion void 33.

Figure 6:
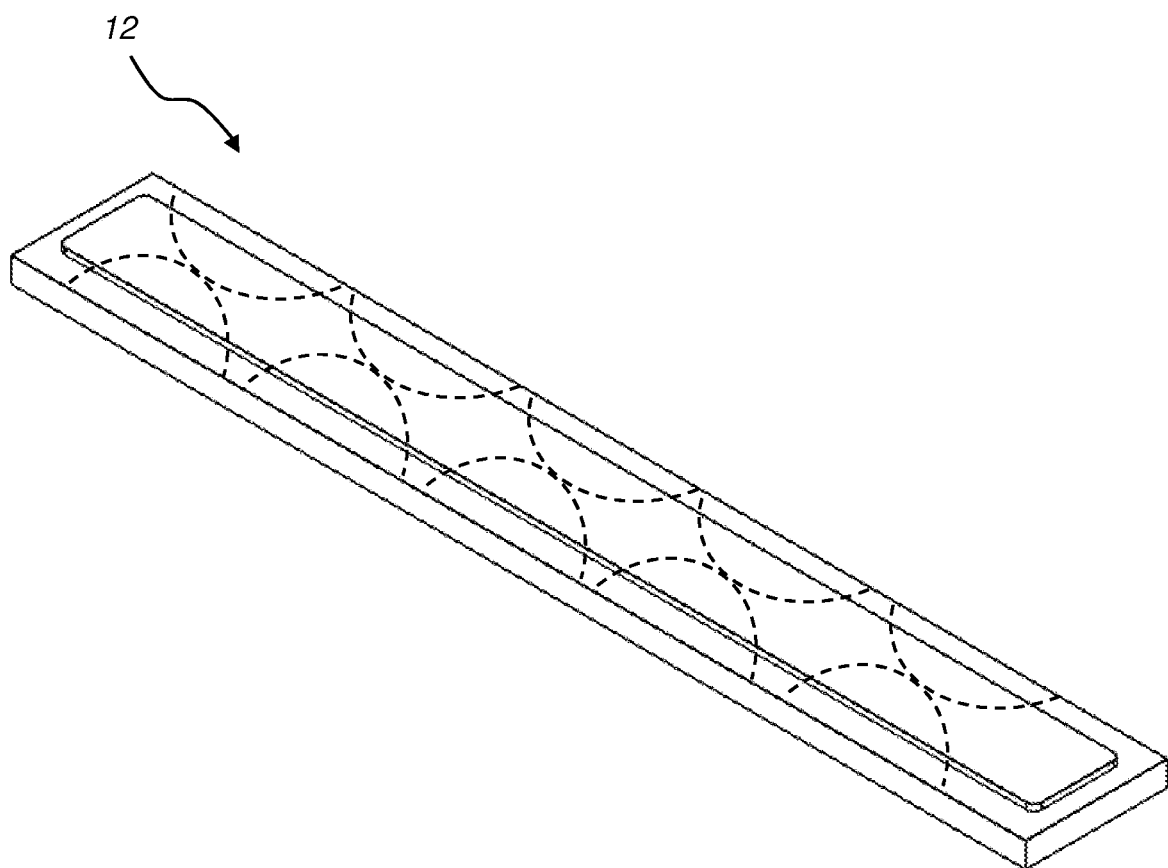
FIG. 6 is a perspective view of the composite titanium body of FIG. 1 showing potential cut marks for forming interbodies from the composite titanium body.

After the composite metal alloy block 12 is formed, one or more composite spinal interbodies may be cut from the composite metal alloy block 12. Alternatively, the portions (including the metal alloy body 10 and porous material 15) may first be cut, and then diffusion bonded together. A single composite metal alloy block 12 as seen in FIG. 6 may be cut into several pieces, with each piece being used to form a composite spinal interbody. It will be appreciated that if the composite metal alloy block 12 is cut as show in dashed lines in FIG. 6, that is if it is cut back-to-back, each spinal interbody will have a front face formed of the non-porous metal alloy body 10, and upper and lower portions formed of the porous material 15, with a medial portion of metal alloy body 10 running from front to back through the spinal interbody.

After cutting the composite metal alloy block 12, each piece of the block may then be further formed into the desired type of spinal interbody, with features added to improve functionality of the composite spinal interbody. Any type of interbody desired may be formed, and the size, shape, and other features of the interbody may be customized.

Figure 7:
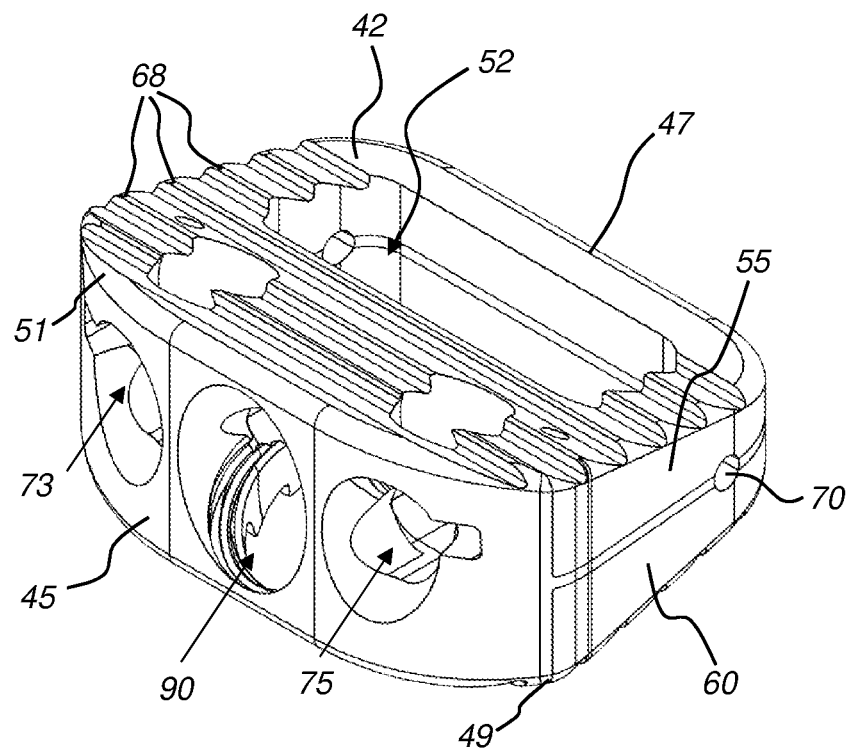
FIG. 7 is a perspective view of an exemplary ALIF interbody formed from a composite titanium body as described herein.
Figure 8:
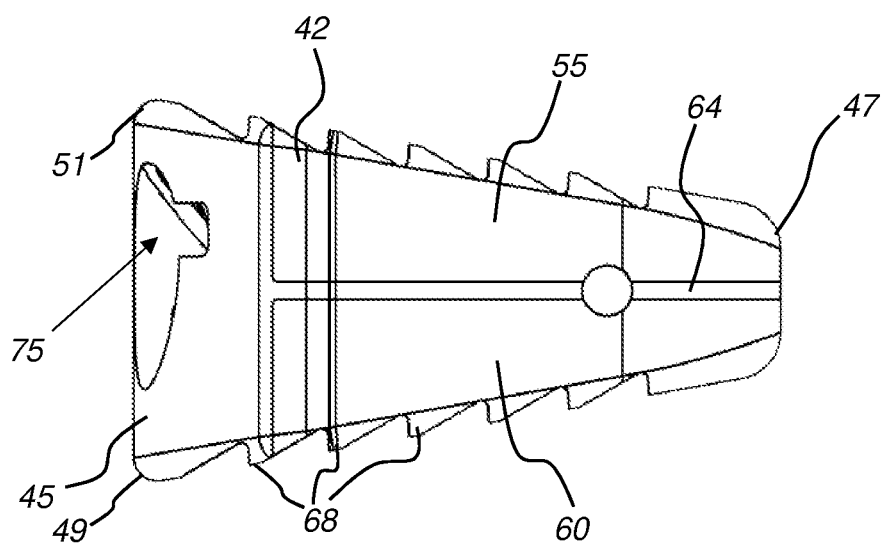
FIG. 8 is a side view of the exemplary ALIF interbody of FIG. 7.

By way of example, an anterior lumbar interbody fusion implant may be formed with a generally trapezoidal shape. One specific example of such an implant 40 is shown in FIGS. 7-8. The implant body 42 is defined by a generally rectangular anterior face 45 and a tapered posterior face 47, with sidewalls extending therebetween. The anterior face 45 may be formed of a metal alloy, for example, if it is cut from a composite metal alloy block 12 as described above. Because the anterior face 45 may have one or more bores or apertures extending therethrough, the use of a metal alloy (rather than a porous metal or porous metal alloy) may reinforce the bores. Compared to porous metal or porous metal alloy, a solid metal alloy anterior face may also be better able to withstand loads applied during implantation.

The anterior face 45 of the implant body 42 extends from a lower surface 49 to an upper surface 51, and from the front of the anterior face 45 towards the tapered posterior face 47. A hollow interior chamber 52 is defined within an inner perimeter of the implant body 42. The anterior face 45 may extend back partway to the hollow interior chamber 52, or nearly to the hollow interior chamber 52, or at least part way from the front end to the hollow interior chamber 52. Additionally, the hollow interior chamber 52 may be filled with cancellous autograft bone, allograft bone, DBM, porous synthetic bone graft substitute, BMP, or combinations of these materials (collectively, bone graft materials), to facilitate osseointegration. In other configurations, the body may be substantially solid and not include the hollow interior chamber 52.

According to some aspects, the osseointegration abilities of implant 40 are further enhanced by coating at least some exterior surfaces with a growth-promoting material, such as crystalline nanoparticles. Suitable crystalline nanoparticles include hydroxyapatite ("HA"), tricalcium phosphate, tetracalcium phosphate, octacalcium phosphate, carbonized HA, fluoro-apatite, magnesium doped apatite, strontium apatite, titanium oxide, yttrium oxide, zirconium oxide and/or combinations thereof. In some configurations, at least part of the exterior surface of the implant 40 is coated with a growth-promoting material. In other configurations, all or nearly all of the exterior surface of the implant 40 is coated with a growth-promoting material.

The implant 40 has an upper portion 55 and a lower portion 60, with both portions tapering towards the posterior face 47. Both the upper portion 55 and lower portion 60 may be formed of porous material 15. Other types of material may also be used. Additionally, a medial portion 64 of the implant body 42 may extend through the middle of the implant body 42 from the anterior face 45 to the posterior face 47. In some configurations, the medial portion 64 is formed of titanium alloy (such as titanium from a titanium body 10), and separates the upper portion 55 and the lower portion 60. The upper portion 55 may be connected to a top surface of the medial portion 64, and the lower portion 60 may be connected to a bottom surface of the medial portion 64. For example, the upper portion 55 and lower portion 60 may be connected to the medial portion 64 by diffusion bonding as discussed above. If the implant body 42 is formed of a composite metal alloy block 12 as described above, each of the upper and lower porous portions 55, 60 may be diffusion bonded to the metal alloy medial portion 64.

In the embodiment shown, the upper and lower surfaces 49, 51 define a plurality of serrations 68. The serrations 68 are defined by both the solid anterior face 45 and the porous upper and lower portions 55, 60. In other configurations the upper and lower surfaces may be relatively smooth, or alternatively may include other bone engaging features configured to reduce slipping or movement of the interbody 40 relative to the vertebrae.

The anterior face 45 of the implant 40 includes a plurality of bores through which screws (not shown in FIGS. 7-8) extend to anchor the implant 40 onto the vertebral body. Additional voids/slots may be provided for receiving an instrument that is used for inserting the implant 40, and may be shaped and sized to mate with an insertion instrument. The implant 40 may further include a transverse aperture 70 towards the posterior face 47. The transverse aperture 70 may provide improved imaging visibility of the implant 40 during surgical procedures to ensure proper implant placement and seating, and may also improve post-operative assessment of implant fusion.

Figure 9:
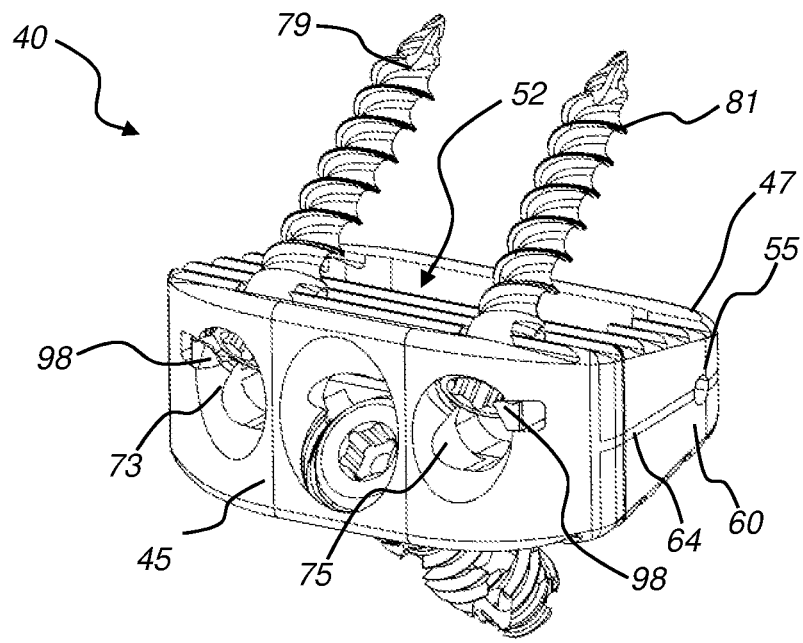
FIG. 9 is a perspective view of the exemplary ALIF interbody of FIG. 7 with screws shown.
Figure 10:
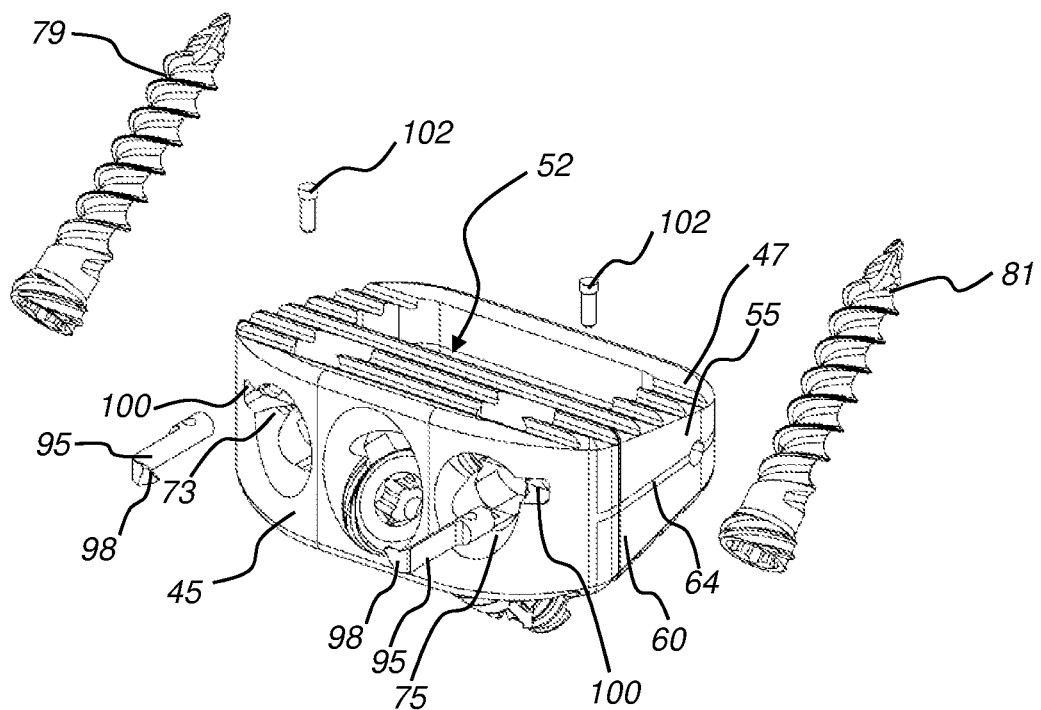
FIG. 10 is an exploded view of FIG. 9.
Figure 11:
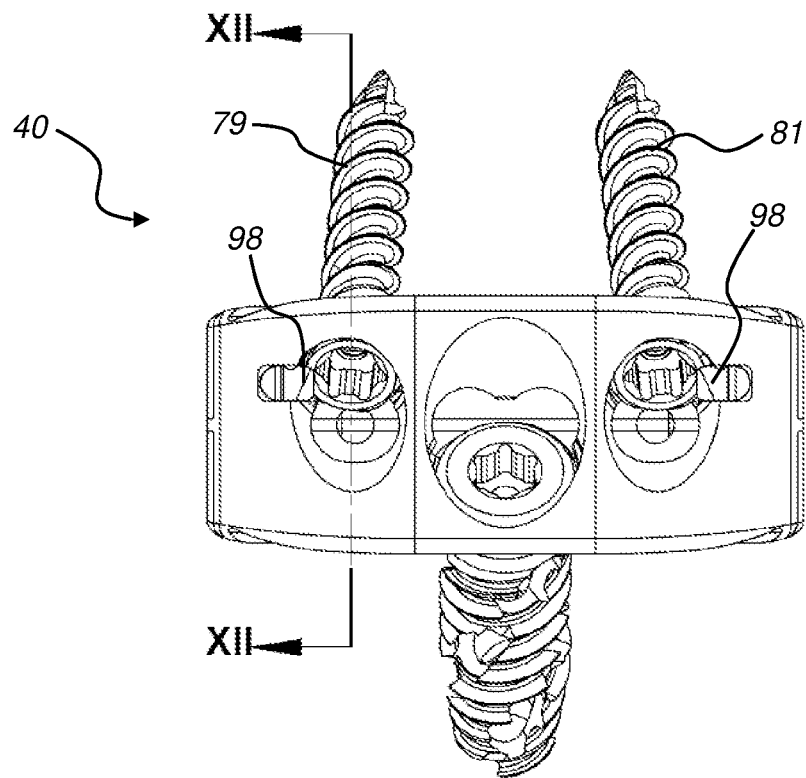
FIG. 11 is a front view of the exemplary ALIF interbody of FIG. 8.

The anterior face 45 of the implant body 42 may include one or more bores for receiving screws to secure the implant body 42 in place. In the exemplary configuration shown in FIGS. 9-10, an angled first bore 73 and an angled second bore 75 may be provided for receiving bone anchors, such as bone screws (bone screws 79, 81 are shown in FIGS. 9-10). While bone screws are shown in this configuration, any type of bone anchor is contemplated. The first and second bores 73, 75 may have any suitable shape, size, and openings to receive the type of bone anchors desired. In the configuration shown in FIGS. 9-10, the first and second bores 73, 75 may be formed such that they extend through the front of the anterior face 45, and out the top surface 51 of the implant body 42 of the implant 40.

Similarly, a third bore 90 may be provided between the first and second bores 73, 75. The third bore 90 may extend from the front of the anterior face 45 and out the lower surface 49 of the body. In the exemplary configuration shown in FIGS. 7-8, the third bore 90 is larger than the first and second bores 73, 75, and designed to receive a cannulated bone screw. In some configurations, only two bores may be provided in the body 42 of the implant 40, and in other configurations, four or more bores may be provided as desired to anchor the implant 40 to vertebrae.

Figure 12:
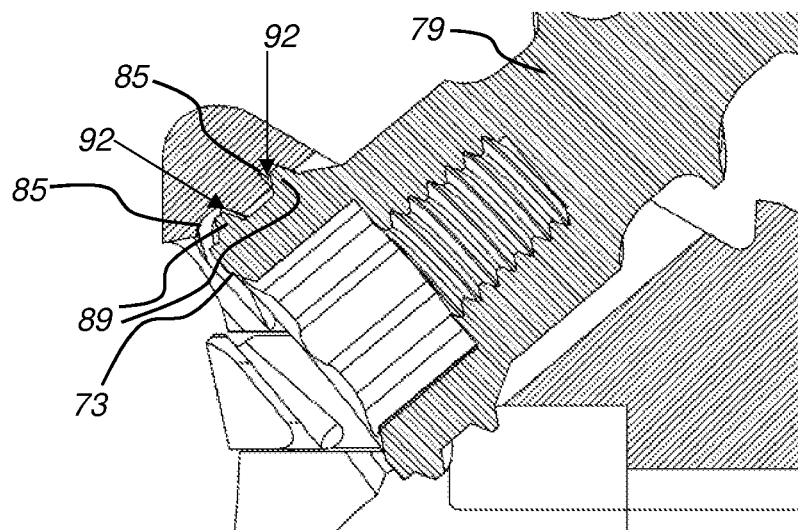
FIG. 12 is a cross-sectional view of the exemplary ALIF interbody of FIG. 8 taken along line XII of FIG. 11.

In some configurations, the one or more bores in the anterior face 45 may also be provided with threads on their inner sides to mate with threads on bone screws. In other configurations, the bores may not be threaded. In one specific configuration of threaded bores, bone screws 79, 81 include heads that are at least partially threaded. The threaded heads of the bone screws 79, 81 and the threads of the first and second bores 73, 75 may be configured to have an amount of clearance between the male and female threads. As seen in the cross-sectional view of FIG. 12, the female threads 85 of the first bore 73 match the pitch of the male threads 89 of the lateral screw 79. A clearance 92 between the female threads 85 and male threads 89 provides a surgeon with control over the angulation of the lateral screw 79 for placement. Providing clearance between the male threads 89 and female threads 85 also allows a surgeon to lag the screws, meaning the surgeon can compress implant 40 to superior and/or inferior vertebrae by rotating bone screws 79, 81 beyond that which is required to close the distance between implant 40 and the superior and/or inferior vertebrae.

In some configurations the implant may also include a locking mechanism to inhibit bone anchor back-out. One exemplary configuration (illustrated in FIGS. 9-10 with two locking mechanisms shown with respect to their placement in an implant 40, and illustrated in FIG. 13 with a locking mechanism shown alone) includes a locking mechanism, generally referenced as 95, that includes a cylinder 93 with an inner end 94 and an outer end 96, with a tab 98 projecting outwardly from the outer end 96. The cylinder 93 of the locking mechanism 95 extends through an axial channel 100 in the implant body 42, and may further be held in place in the axial channel 100 by a vertical pin 102 (FIG. 10). The channel 100 is proximal to a bore for a bone anchor (such as bores 73, 75) so the outwardly projecting tab 98 of the locking mechanism 95 extends into the bore, as described in more detail below. The channel 100 may extend from the anterior face 45 rearwardly, and may extend substantially normal from a line tangent to the anterior face 45, or alternatively, may extend at an angle. The axial channel 100 may be sized with a diameter slightly greater than a diameter of the cylinder 93, such that the cylinder 93 of the locking mechanism 95 fits snugly within the channel 100. A pin 102 may be inserted vertically through the top surface 51 of the implant body 42, and into a vertical bore 97 in inner end 94 the cylinder 93 of the locking mechanism 95 to ensure the locking mechanism 95 is held securely in place within the implant body 42.

Figure 13:
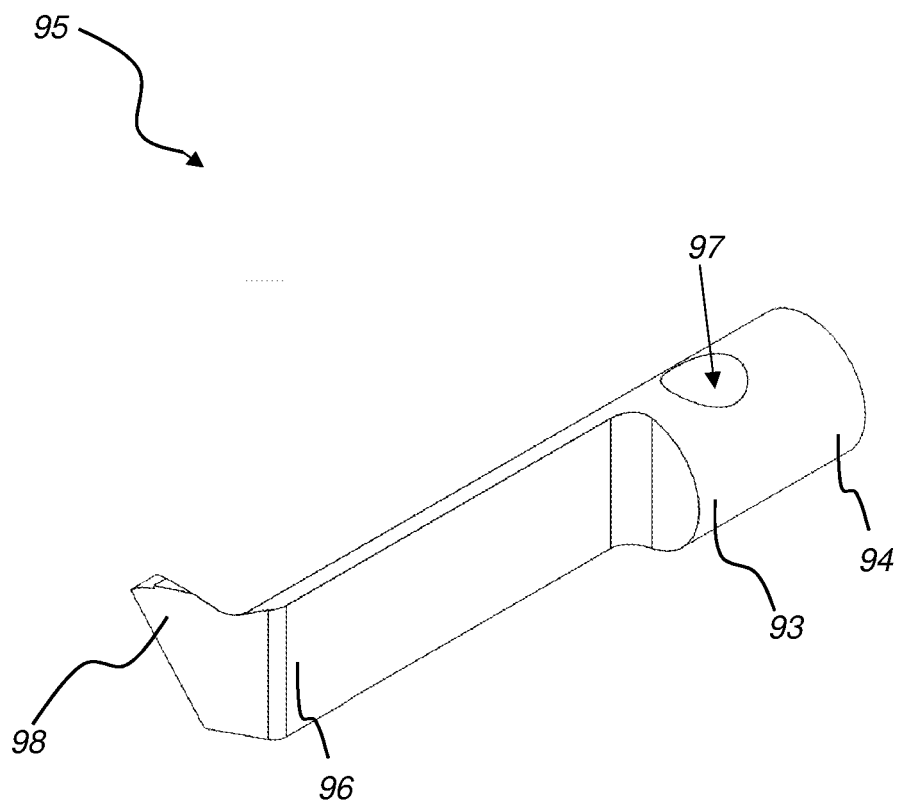
FIG. 13 is a perspective view of an exemplary locking mechanism.

As seen in FIG. 13, the exemplary embodiment of the locking mechanism 95 includes an outwardly extending tab 98 on the outward end 96. When the cylinder of the locking mechanism 95 is in place in the channel 100, the outwardly extending tab 98 extends into a bore for receiving a bone screw. The tab 98 may also have a front, angled face. Additionally, a portion of the cylinder 93 may be cut away proximal to the outward end 96. The angled face and the cut-away of the cylinder may allow the tab 98 to be deformed outwardly away from the bore and allow a bone anchor to pass by the tab 98 as the anchor is inserted (rather than the tab 98 blocking the bore). Once the head of the bone anchor passes the tab 98, the tab 98 is biased back into place within the bore, engaging the head of the screw to prevent the screw from backing out.

In use, a bone screw 79 is first introduced into bore 73, until the head of the bone screw pushes against the outwardly projecting tab 98 of the locking mechanism 95. Due to the angled face of the outwardly projecting tab 98, the head of the screw may push the tab 98 outwardly and move past tab 98. As the head of the screw clears the tab 98, the tab 98 is biased back into place (now between the head of the bone screw and the entrance of bore 73) and engages the head of the screw to inhibit screw back-out by physically blocking the bone screw 79 from moving back out of the bore 73. It will be appreciated that other types of locking mechanisms may also be used to inhibit screw back-out.

Figure 14:
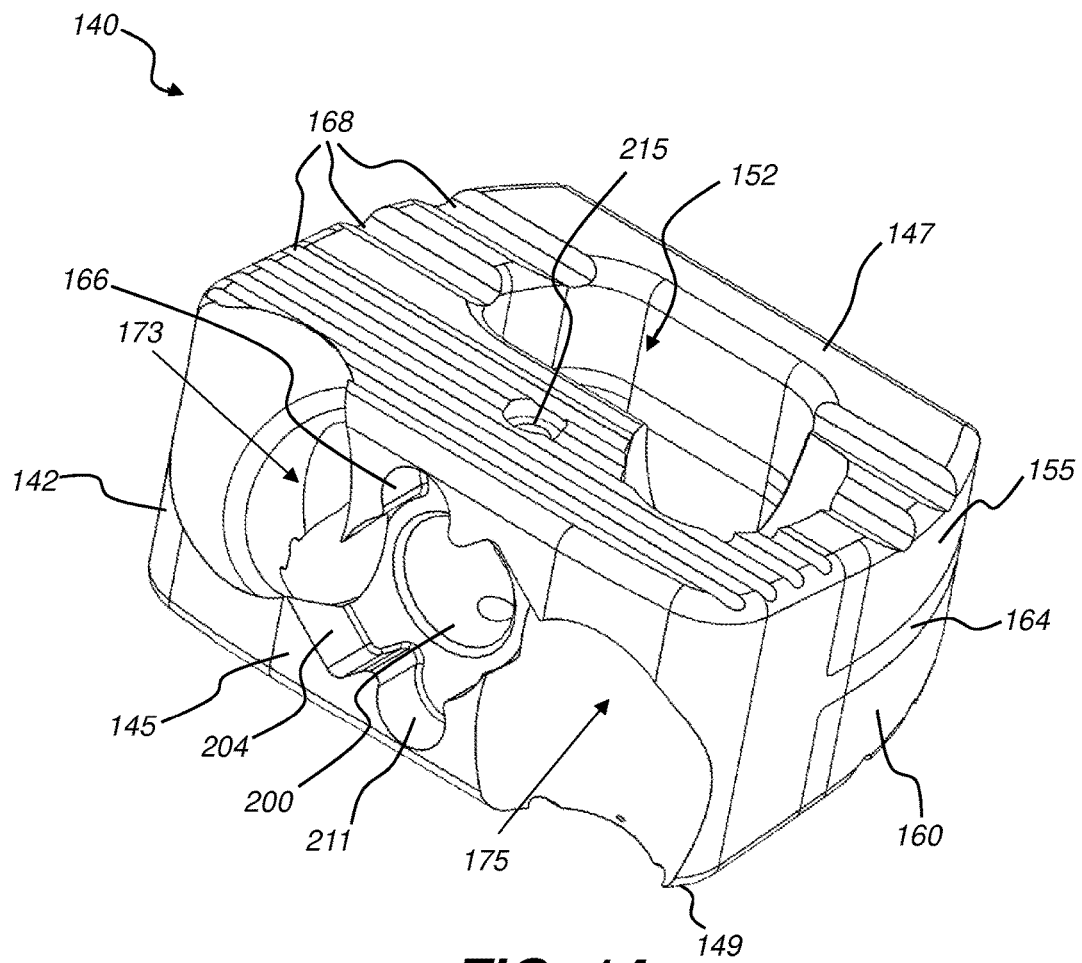
FIG. 14 is a perspective view of an exemplary cervical interbody formed from a composite titanium body as described herein.
Figure 15:
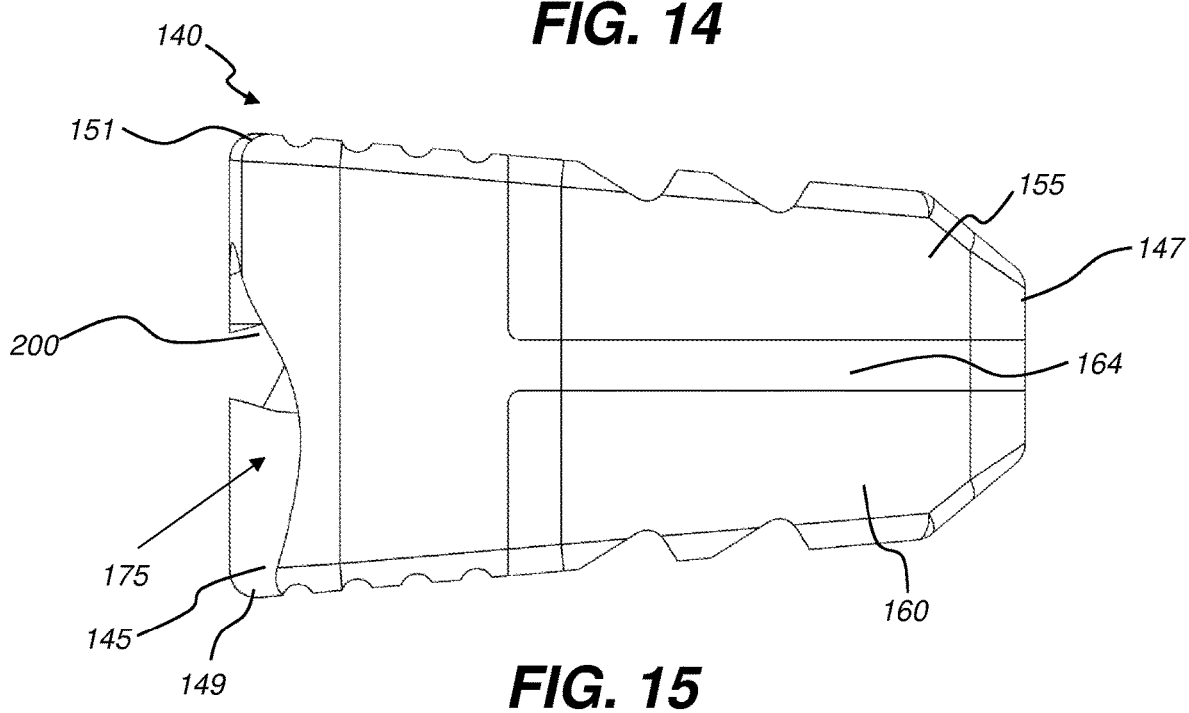
FIG. 15 is a side view of the exemplary cervical interbody of FIG. 14.

Turning now to FIGS. 14-15, an exemplary configuration of a cervical implant 140 is shown, which may be formed from a composite metal alloy block 12 as described herein. The cervical implant 140 may include a body 142 having a generally D-shape. The implant body 142 is defined by a generally rectangular anterior face 145 and a tapered posterior face 147, with sidewalls extending therebetween. The anterior face 145 may be formed of titanium alloy, for example, if it is cut from a composite metal alloy block 12 as described above. The anterior face 145 of the body 142 extends from a lower surface 149 to an upper surface 151, and from the front of the anterior face 145 towards the tapered posterior face 147. A hollow interior chamber 152 is defined within an inner perimeter of the implant body 142. The metal alloy anterior face 145 may extend back partway to the hollow interior 152, or nearly to the hollow interior 152, or at least part way from the front end to the hollow interior 152. Additionally, the hollow interior 152 may be filled with cancellous autograft bone, allograft bone, DBM, porous synthetic bone graft substitute, BMP, or combinations of these materials (collectively, bone graft materials), to facilitate osseointegration. In other configurations, the body is solid and does not include the hollow interior 152.

The cervical implant 140 has an upper portion 155 and a lower portion 160, with both portions tapering towards the posterior face 147. Both the upper portion 155 and lower portion 160 may be formed of porous material 15. Other types of material may also be used. Additionally, a medial portion 164 of the body 142 may extend through the middle of the body 142 from the anterior face 145 to the posterior face 147. In some configurations, the medial portion 164 is formed of a metal alloy (such as titanium from a titanium body as described above), and separates the porous upper portion 155 and the porous lower portion 160. The upper portion 155 may be connected to a top surface of the medial portion 164, and the lower portion 160 may be connected to a bottom surface of the medial portion 164. For example, the upper portion 155 and lower portion 160 may be connected to the medial portion 164 by diffusion bonding as discussed above. If the implant body 142 is formed of a composite metal block 12 as described above, each of the upper and lower porous portions 155, 160 may be diffusion bonded to the metal alloy medial portion 164.

In the specific configuration shown, the lower surface 149 and upper surface 151 of the body 142 define a plurality of indentations 168. The indentations 168 are defined by both the solid anterior face 145 and the porous upper and lower portions 155, 160. In other configurations the upper and lower surfaces may be relatively smooth, or alternatively may include other bone engaging features configured to reduce slipping or movement of the cervical implant 140 relative to the vertebrae.

The anterior face 145 of the implant 140 may includes a plurality of voids through which screws (not shown in FIGS. 14-15) extend to anchor the implant onto the cervical spine. Additional voids/slots may be provided for receiving an instrument that is used for inserting the cervical implant 140 and/or for receiving a locking mechanism 195 as described below. In the exemplary configuration of FIGS. 14-15, shaped void 200 is provided for receiving a locking mechanism, and cut-outs 211 are provided for receiving an insertion instrument.

The anterior face 145 of the implant body 142 may include one or more bores for receiving screws to secure the implant body 142 in place. In the exemplary configuration shown in FIGS. 14-15, an angled first bore 173 and an angled second bore 175 may be provided for receiving cervical bone screws (cervical bone screws 179, 181 are shown in FIGS. 16-19). The first and second bores 173, 175 may have any suitable shape, size, and openings to receive the type of bone screws or other type of bone anchor desired. In the configuration shown in FIGS. 14-15, the first bore 173 is formed such that it extends through the front of the anterior face 145, and out the bottom surface 149 of the implant 140. The second bore 175 is formed such that it extends through the front of the anterior face 145, and out the top surface 151 of the body 142 of the cervical implant 140. In some configurations, the first and second bores 173, 175 may also be provided with threads to mate with threads on bone screws 179, 181. In other configurations, the first and second bores 173, 175 may not be threaded.

Where a threaded engagement between bone screws 179, 181 and body 142 is desired, the engaging threads on bone screws 179, 181 may be located at least partially on the respective heads of bone screws 179, 181. In some embodiments, the threaded heads of the bone screws 179, 181 and the threads of the first and second bores 173, 175 may be configured to have an amount of clearance between the male and female threads. Incorporating a clearance between the threads on bone screws 179, 181 and threads on bores 173, 175 may provide a surgeon with control over the angulation of bone screws 179, 181 and may also a surgeon to lag the screws, meaning the surgeon can compress implant 140 to superior and/or inferior vertebrae by rotating bone screws 179, 181 beyond that which is required to close the distance between implant 140 and the superior and/or inferior vertebrae.

Figure 16:
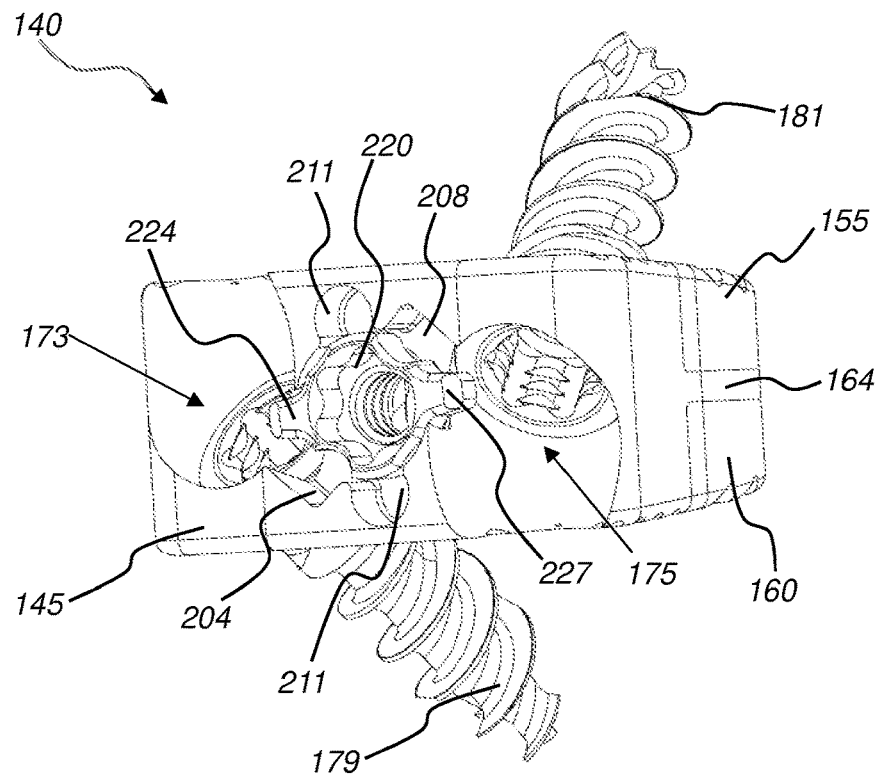
FIG. 16 is a perspective view of the exemplary cervical interbody of FIG. 14 with screws shown.
Figure 17:
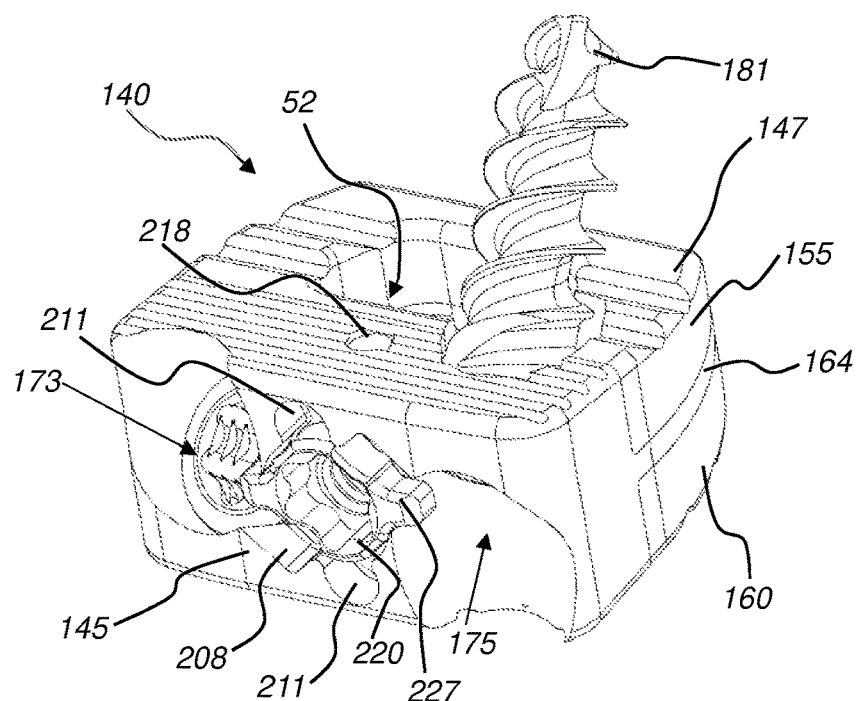
FIG. 17 is a top perspective view of the exemplary cervical interbody of FIG. 14 with screws shown.

The cervical implant 140 may also be provided with one or more locking mechanisms to ensure that bone anchors do not back-out. As seen in FIGS. 16-20, a locking mechanism 195 may be provided. In the specific configuration shown, the anterior face 145 of the cervical implant body 142 may include a shaped void 200 for receiving the locking mechanism 195. The shaped void 200 may be located between the first bore 173 and the second bore 175. The shaped void 200 may comprise a first slot 204 proximal to and at least partially extending into the first bore 173, and a second slot 208 proximal to and at least partially extending into the second bore 175 (FIG. 16). Each of the first slot 204 and second slot 208 may receive the arms of the locking mechanism 195 as described below. The shaped void 200 may also include one or more additional cut-outs 211 for receiving an insertion tool. (Exemplary insertion tools are discussed below with regard to FIGS. 21A-27.) The body 142 may also include a vertical opening 215 extending from the upper surface 151 for receiving a vertical pin 218 to hold the locking mechanism 195 in place.

The locking mechanism 195 may consist of a rotatable blocker 220 receivable in the shaped void 200 of the implant body 142. The rotatable blocker 220 may include a first outwardly extending arm 224 and a second outwardly extending arm 227. In some configurations, the first and second arms may be directly opposed to each other. In other configurations, one arm or three or more arms may be provided. The first outwardly extending arm 224 may rotate within the first slot 204 of the shaped void 200, and the second outwardly extending arm may rotate within the second slot 208 of the shaped void 200. The rotatable blocker 220 may have a first, open position wherein bone anchors may be inserted and a second, closed position wherein bone anchors may not be inserted. In the specific configuration shown in FIGS. 16-19, the first slot 204 allows the first outwardly extending arm 224 to rotate from the closed position at about 180 degrees to the open position at about 270 degrees. Similarly, the second slot 208 allows the second outwardly extending arm 227 to rotate from the closed position at about 0 degrees to the open position at about 45 degrees. The rotatable blocker 220 extends into the one or more bores in the second, closed position but does not extend into the one or more bores in the first, open position. In the closed position, each of the first and second outwardly extending arms 224, 277 at least partially extends into the first and second bores 173, 175 respectively. Because of this at least partial blockage of the bores, any bone anchors placed within the bores cannot back-out because they are physically blocked by the outwardly extending arms of the rotatable blocker 220.

To hold the rotatable blocker 220 in place on the body 142 of the cervical implant 140, the body 142 may include a vertical opening 215 extending downwardly from the upper surface 151 for receiving a vertical pin 218. The rotatable blocker may include an aperture 225 or slot for receiving vertical pin 218 (see FIG. 20). The aperture 225 may allow the rotatable blocker 220 to be held in place even as it is rotated between the open and closed positions with respect to the vertical pin 218.

In use, a surgeon may first place the cervical implant body 142. For example, an insertion tool having a geometry that mates with the cut-outs 211, and/or screws that mate with an optionally threaded portion of the rotatable blocker 220. Next, the surgeon may ensure that the rotatable blocker 220 is in the unlocked position, with each of the first and second outwardly extending arms rotated out of the bores. With the rotatable blocker in the open position, the surgeon may introduce one or more bone anchors through bores. When the surgeon is satisfied that the bone anchors and body of the implant are correctly placed, the surgeon may then rotate the blocker 220 to the closed position. Again, an insertion tool may be used to rotate the blocker. In the closed position, the outwardly extending arms of the rotatable blocker may prevent back-out of bone anchors from the bores.

Figure 21A:
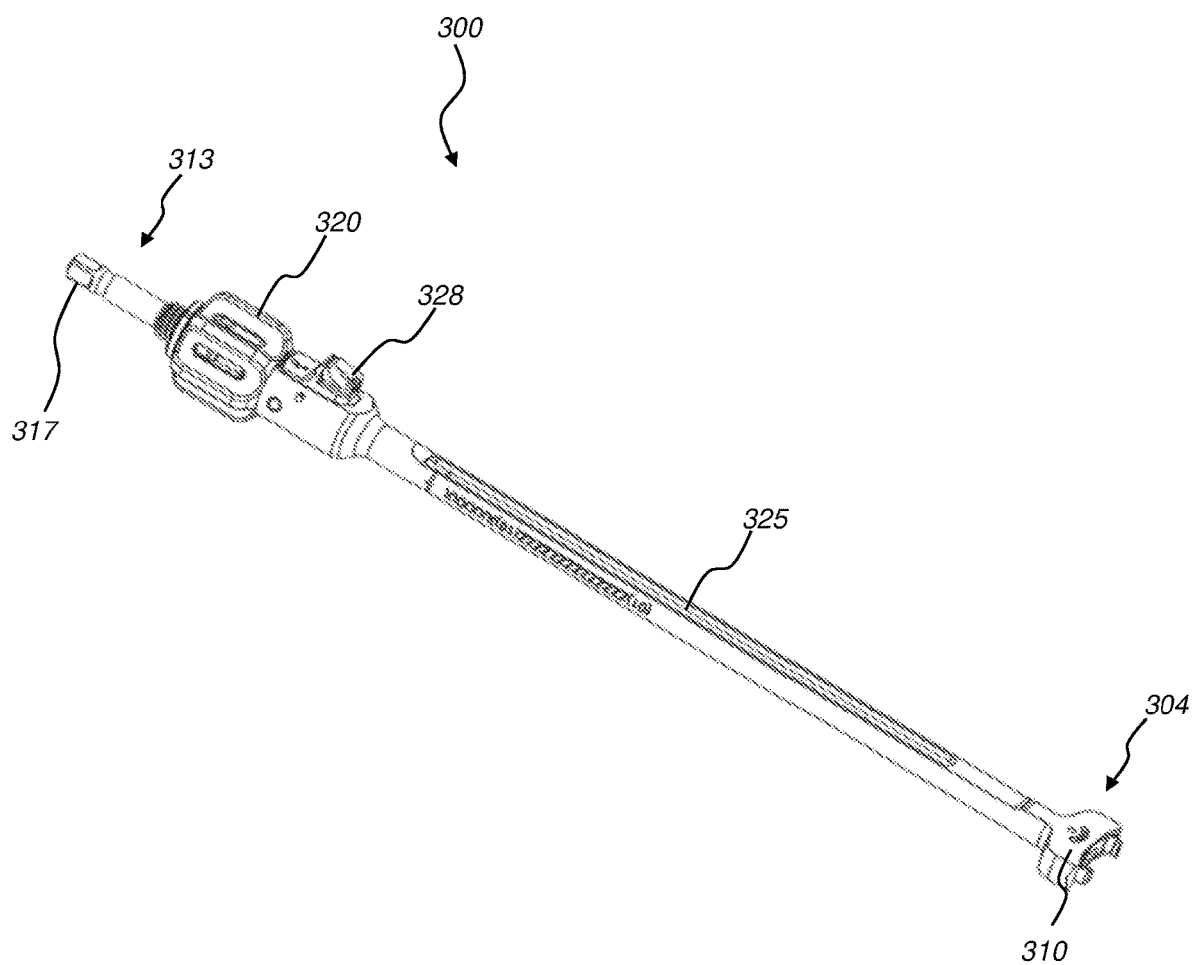
FIG. 21A is a perspective view of an exemplary insertion tool.
Figure 21B:
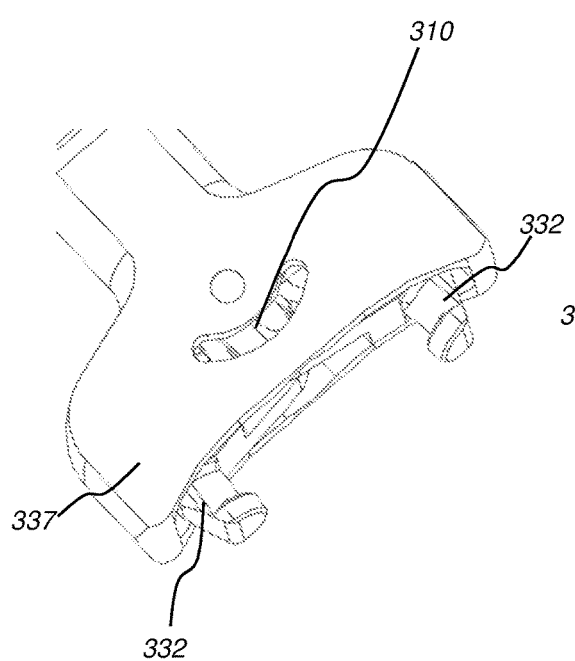
FIG. 21B is an enlarged view of the distal end of the insertion tool of FIG. 21A.

FIG. 21A illustrates one aspect of an insertion tool 300 that has a distal end 304 configured to engage with a suitable implant, such as implant 40 discussed herein, with an implant engagement mechanism 310 (shown in greater detail in FIG. 21B). Insertion tool 300 further includes a proximal end 313 with a handle engagement portion 317 and a knob 320 configured to engage and disengage the implant. Between the proximal and distal ends is an elongate shaft 325. The proximal end 313 further includes a locking mechanism 328 configured to optionally maintain implant engagement mechanism 310 in a locked configuration. Knob 320 is mechanically connected to an inner shaft contained within elongate shaft 325, such that rotation of knob 320 causes the inner shaft to translate relative to elongate shaft 325 thereby causing implant engagement mechanism 310 to either open or close depending on which direction the inner shaft is translated.

Figure 21C:
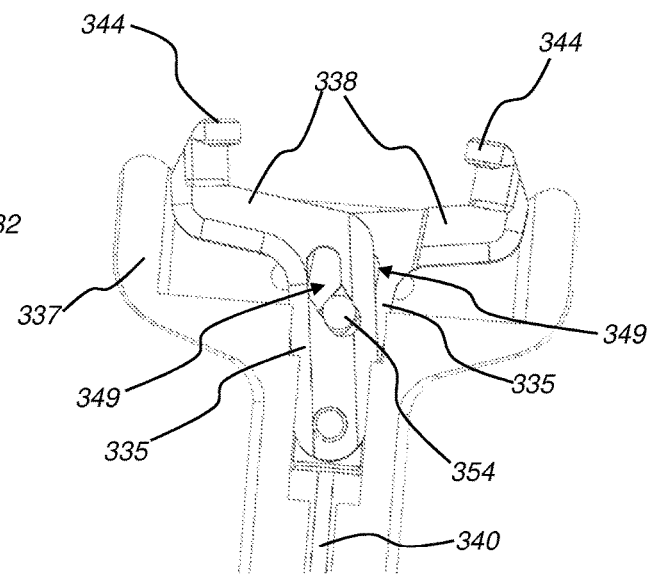
FIG. 21C is a cross-sectional view of the distal end of the insertion tool of FIG. 21A.

FIGS. 21B and 21C illustrate in better detail some features of implant engagement mechanism 310, such as the lateral tongs 332 that are each defined by a base portion 335, an arm 338, and an inward projection 344 (FIG. 21C). Implant engagement mechanism 310 is contained within a housing 337 and, as suggested above, is mechanically connected to an inner shaft 340. Each base portion 335 includes an angled or bent slot 349 that engages a pin 354 that is positioned in and in a fixed relation to housing 337. Distal translation of inner shaft 340 pushes each base portion 335 distally causing each base portion 335 to travel along a path defined by slots 349 as they move along pin 354. In this illustrated design, distal translation of inner shaft 340 causes implant engagement mechanism 310 to open, which may be required to accept an implant.

Securing the implant to insertion tool 300 may be achieved by rotating knob 320 to cause proximal translation of inner shaft 340 and resulting closure of implant engagement mechanism 310 around at least a portion of the implant, which places inward projections 344 into engaging contact with corresponding surfaces on the implant. One skilled in the art will appreciate that the opening and closing of implant engagement mechanism 310 involves proximal and distal translation, respectively, of the mechanism. Such translation may be useful when disengaging the implant in a desired location of a patient's spine. In other words, when the desired location has been achieved, insertion tool 300 is disengaged by opening implant engagement mechanism 310, which causes the mechanism to slightly push distally against the implant thereby pushing the mechanism proximally away from the implant as it releases the implant. Such a configuration may advantageously aid a surgeon in removing insertion tool 300 while maintaining the implant in its desired location.

Figure 22A:
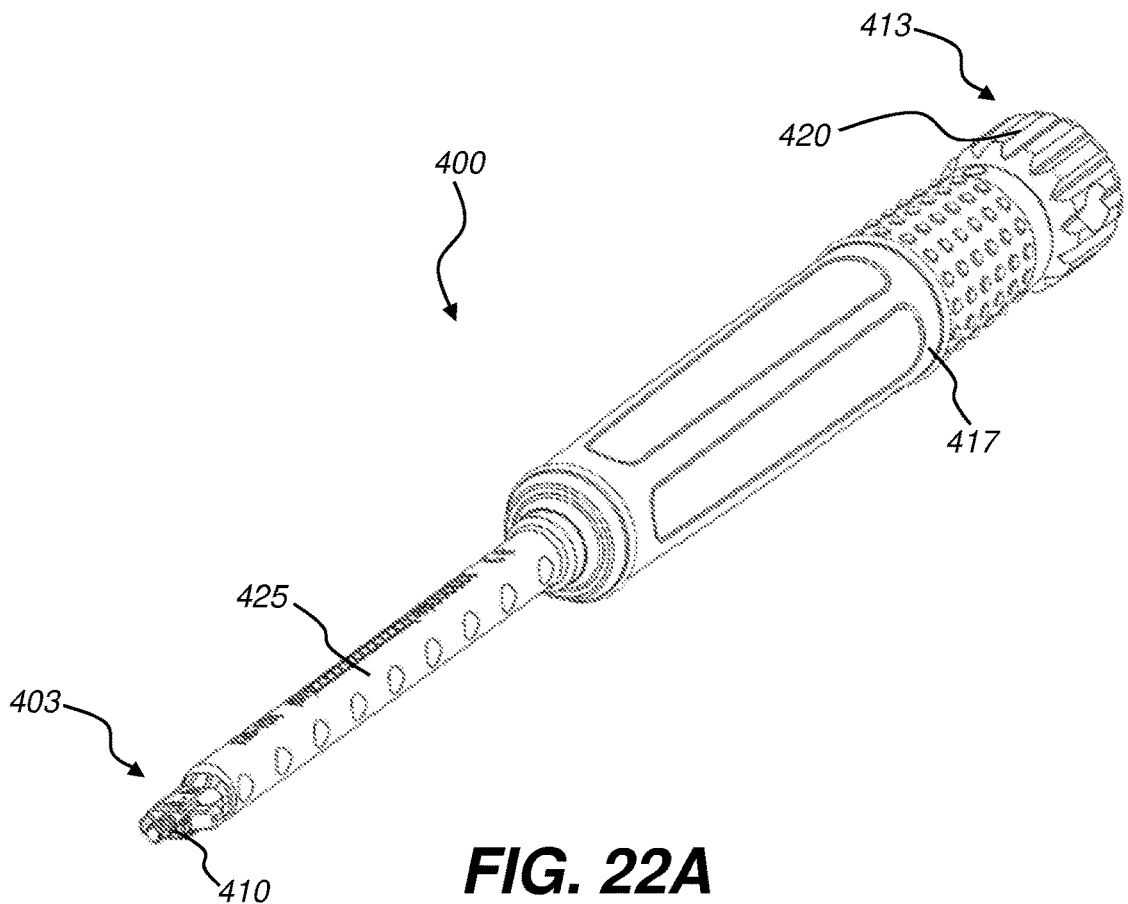
FIG. 22A is a perspective view of another exemplary insertion tool.

FIG. 22A illustrates another aspect of an insertion tool 400, which includes at its proximal end 413 a handle 417 and knob 420 and at its distal end an implant engagement mechanism 410. An elongate shaft 425 connects the proximal and distal ends.

Figure 22B:
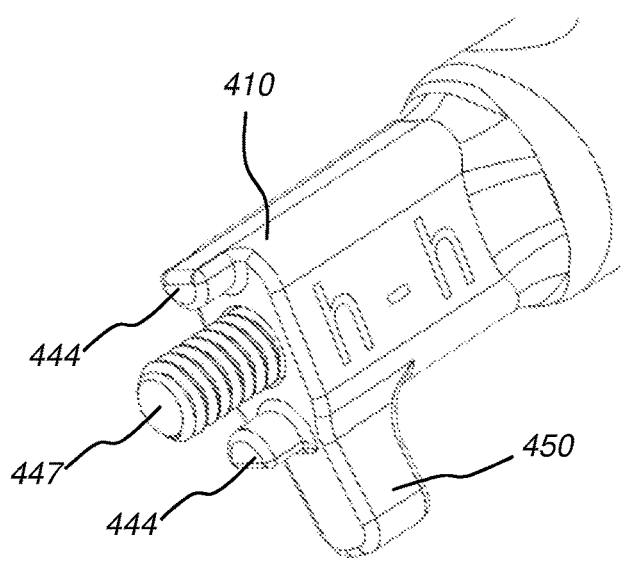
FIG. 22B is an enlarged view of the distal end of the insertion tool of FIG. 22A.

FIG. 22B is an enlarged view of the distal end 404 of insertion tool 400 and illustrates that implant engagement mechanism 410 includes a pair of distally extending prongs 444 and an engagement rod 447. Engagement rod 447 is the distal end of a rod that extends up through elongate shaft 425 to mechanically connect to knob 420 such that rotation of knob 420 rotates engagement rod 447 that includes threads that engage with a threaded bore in an implant, such as the threaded bore found in rotatable blocker 220 of cervical implant 140. Prongs 444 are designed to engage with a corresponding geometry on an implant and to stabilize the implant so that engagement rod 447 can thread into the implant. For example, prongs 444 may be configured to engage with cut-outs 211 on implant 140 or a similar geometry on a different implant.

Figure 18:
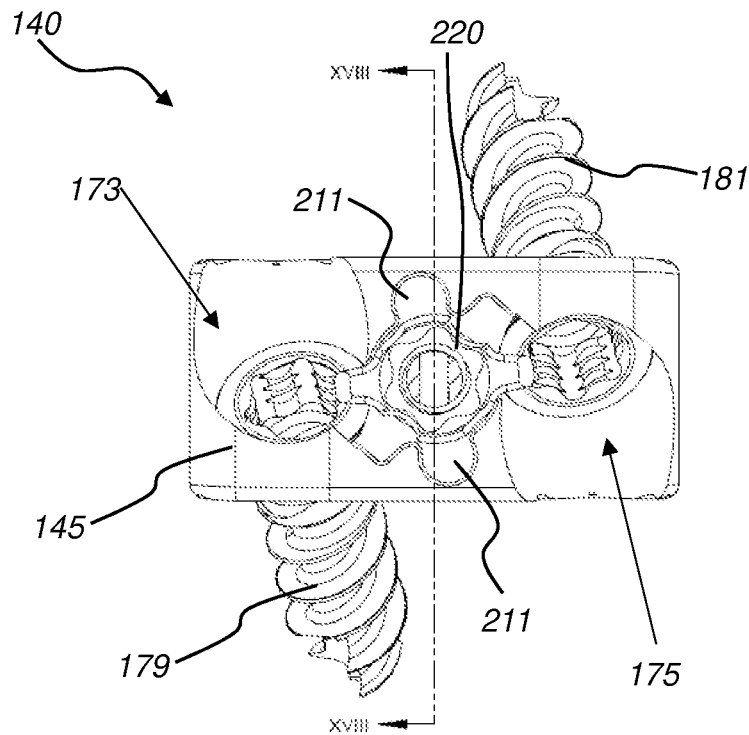
FIG. 18 is a front view of the exemplary cervical interbody of FIG. 14 with screws shown.
Figure 19:
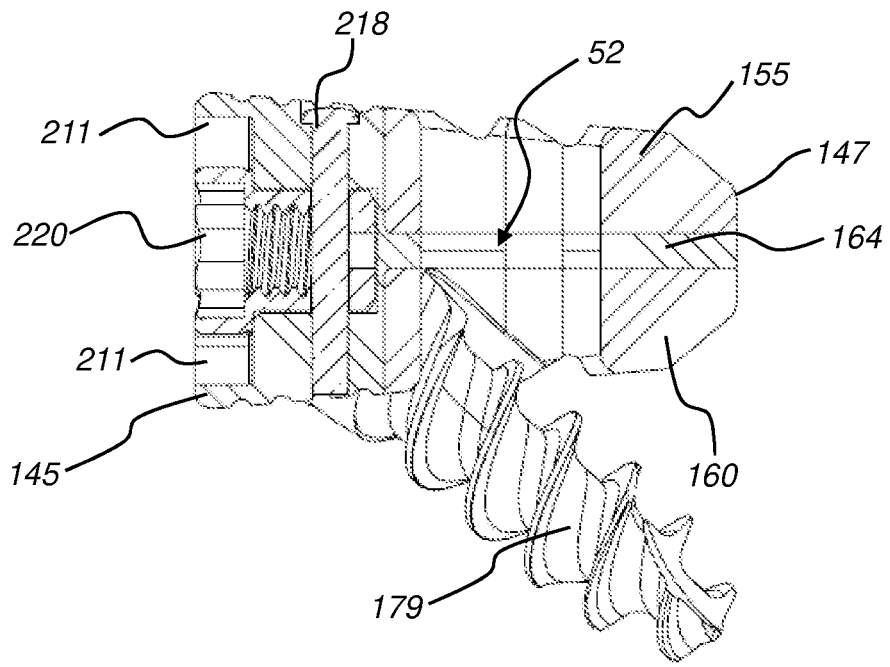
FIG. 19 is a cross-sectional view of the cervical interbody of FIG. 14 taken along line XVIII of FIG. 18.
Figure 20:
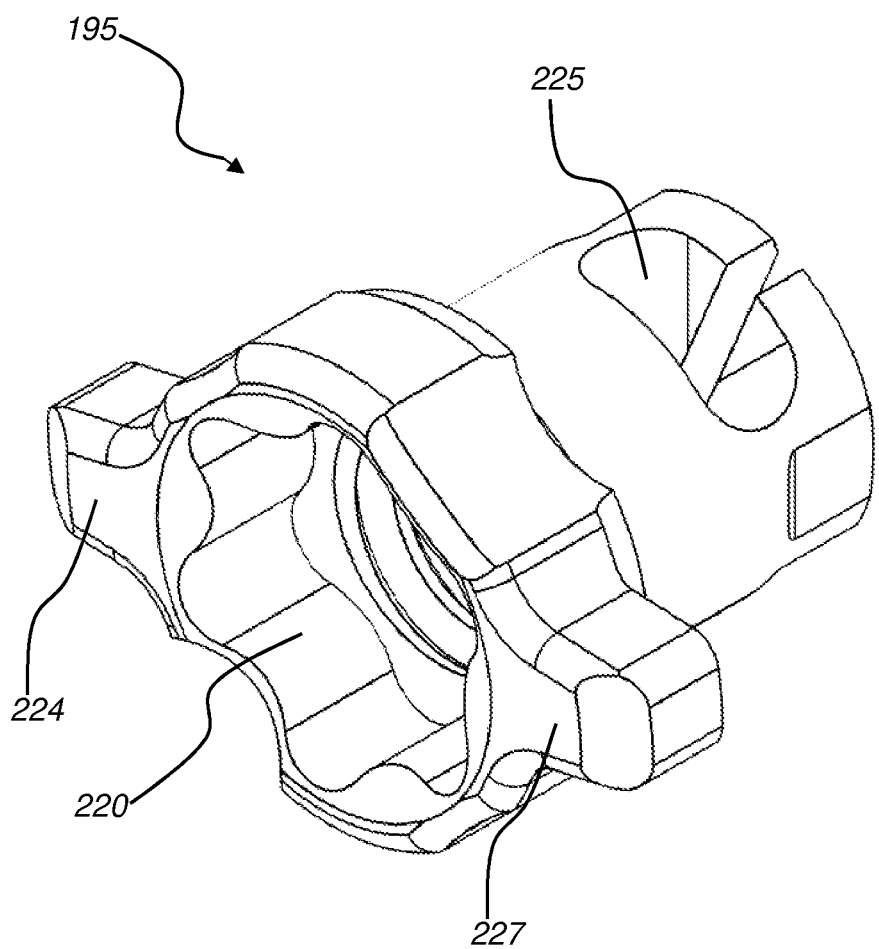
FIG. 20 is a perspective view of another exemplary locking mechanism.

According to some aspects, prongs 444 are configured to prevent the rotation of a locking mechanism of the implant while insertion tool 400 is engaged with the implant. For example, FIG. 18 illustrates that rotatable blocker 220 includes a pair of scalloped edges that align with cut-outs 211, such that when prongs 444 are inserted therein, rotation of rotatable blocker 220 is either prevented or made more difficult. Such a design may advantageously prevent rotatable blocker from inadvertently closing prior to the insertion of bone screws 179, 181.

FIG. 22B also illustrates that the distal end 404 of insert tool 400 includes a stop 450, which in this illustrated aspect is positioned so that a distal surface of stop 450 is contiguous with a distal surface of the implant engagement mechanism 410. Stop 450 may be used to guide a surgeon or other user in the placement and positioning of an implant in an intervertebral disc space. For example, stop 450 may be used to abut against the superior or inferior vertebral body so as to not insert an implant too far into the intervertebral disc space. A skilled artisan will understand, then, that stop 450 may be positioned at the distal-most position of insertion tool 400 or it may be positioned slightly proximal to the distal-most position so as to allow a surgeon to insert an implant slightly further into the disc space. A skilled artisan will also understand that insertion tool 400 could include no stop at all so at to maximize the maneuverability for the surgeon or user.

Figure 23A:
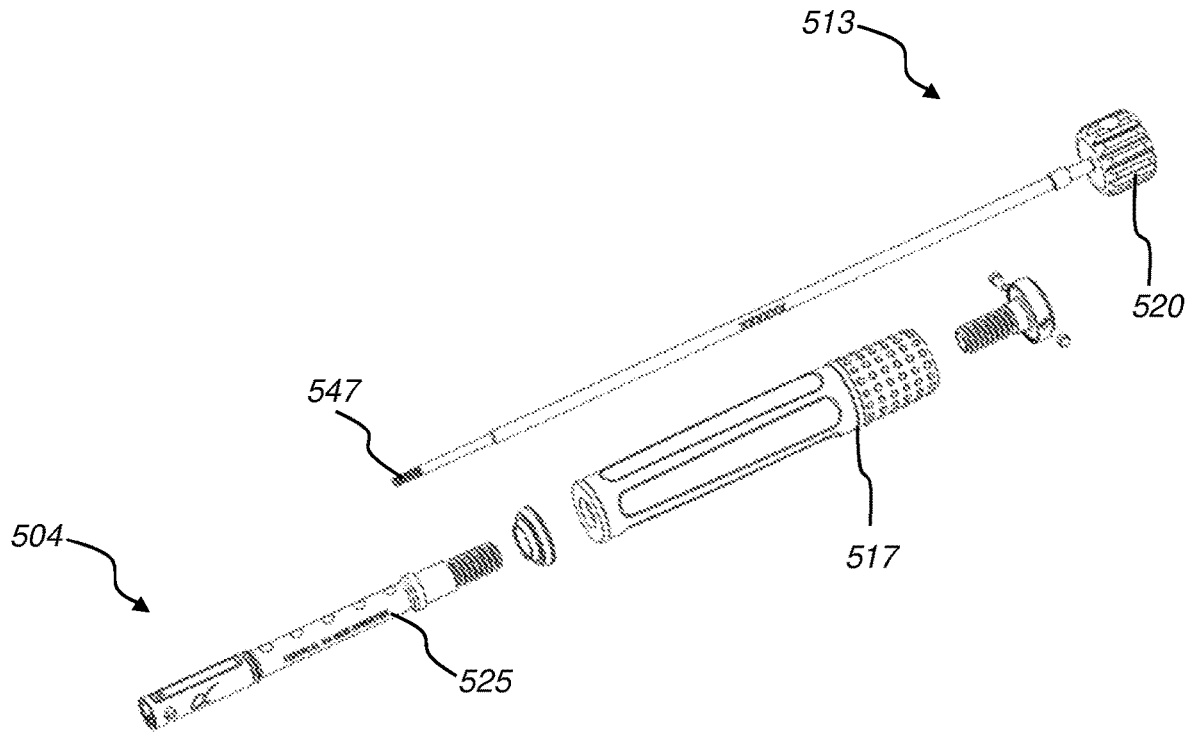
FIG. 23A is a perspective, exploded view of another exemplary insertion tool.
Figure 23B:
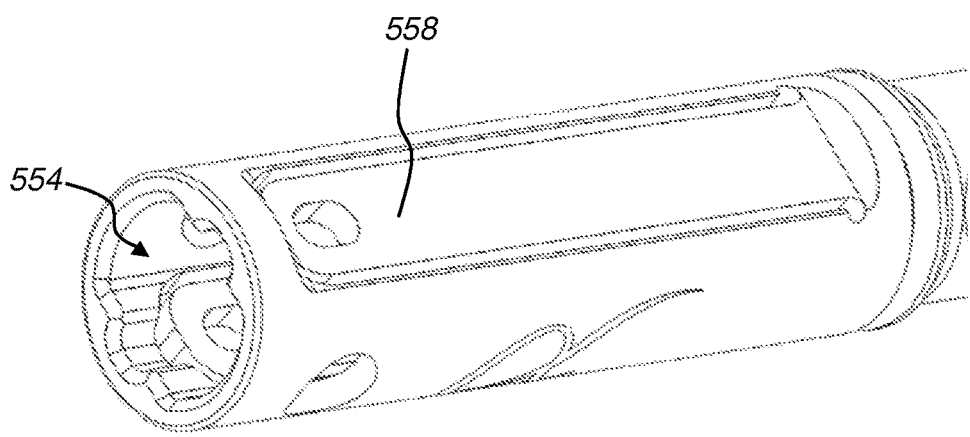
FIG. 23B is an enlarged view of the distal end of the insertion tool of FIG. 23A.

FIG. 23A illustrates another aspect of an insertion tool 500 that, similar to insertion tool 400, includes a proximal end 513 having a handle 517 and a knob 520; however, the distal end 504 of insertion tool 500 is configured to receive a variety of modular tips that are detailed in greater detail below (see FIGS. 24-26). Specifically, insertion tool 500 has an elongate shaft 525 extending from handle 517, and at the distal end of elongate shaft 525 is an opening 554 configured to receive an extension of a modular tip. FIG. 23B illustrates that opening 554 includes a pair of flexible members 558 that releasably receive respective projections on the extension of the modular tip. As with insertion tool 400, insertion tool 500 includes an engagement rod 547 mechanically connected to knob 520 and extending distally through elongate shaft 525. However, unlike with insertion tool 400, engagement rod 547 extends well beyond the distal end of elongate shaft 525 so as to extend through and beyond whatever modular tip is secured to insertion tool 500 at opening 554.

Figure 24:
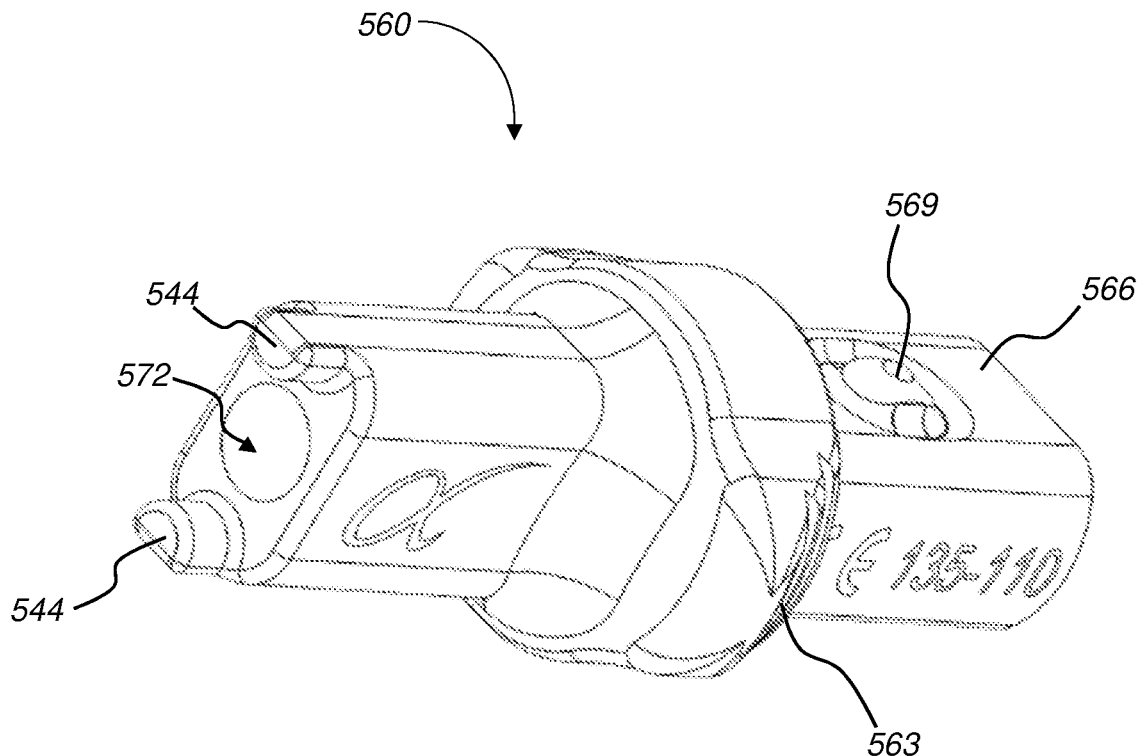
FIG. 24 is a perspective view of an exemplary modular tip to be used with the insertion tool of FIG. 23A.

FIG. 24 illustrates an aspect of a modular tip 560. Although modular tip 560 resembles the distal end of insertion tool 400 in that it includes a pair of distally extending projections 544; however, modular tip 560 does not include a stop. Moreover, modular tip 560 includes a pair of gripping surfaces 563 to facilitate the attachment and detachment of modular tip 560 from opening 554 of insertion tool 500. Modular tip 560 further includes an extension 566 having a pair of projections or nubs 569 configured to be received by flexible members 558 of insertion tool 500. Modular tip 560 also includes a lumen 572 running from the distal end to the proximal end, lumen 572 configured to receive engagement rod 547 of insertion tool 500.

Figure 25:
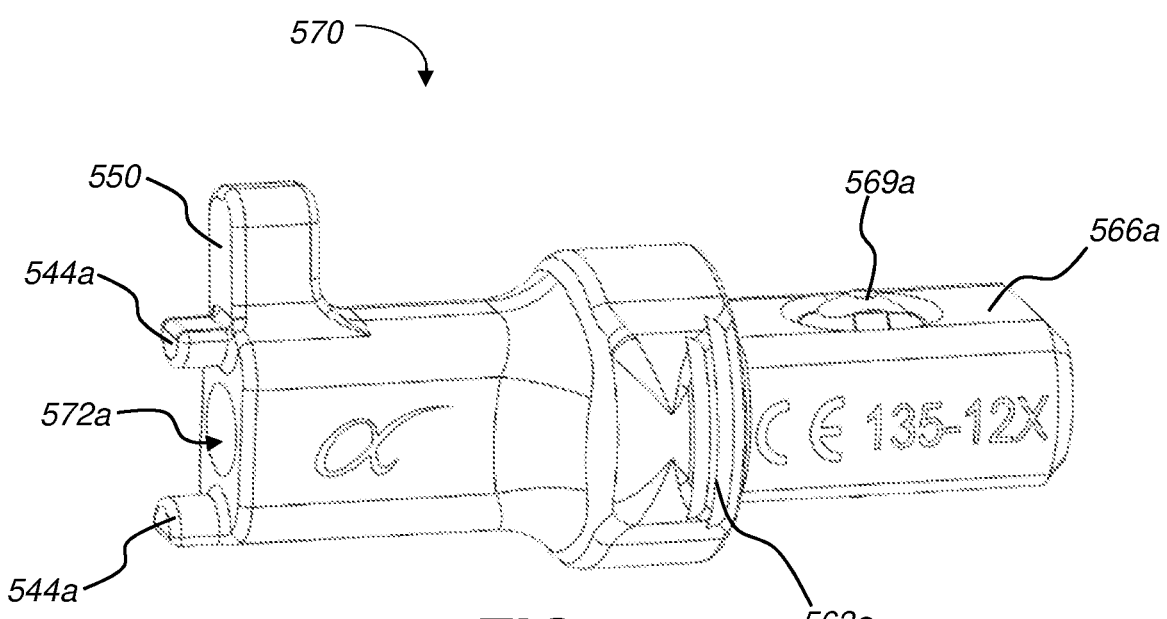
FIG. 25 is a perspective view of another exemplary modular tip to be used with the insertion tool of FIG. 23A.

FIG. 25 illustrates an aspect of another modular tip 570 that, similar to modular tip 560, includes a pair of distally extending projections 544*a*, a pair of gripping surfaces 563*a*, an extension 566*a* with nubs 569*a*, and a lumen 572*a* for receiving engagement rod 547. However, modular tip 570 includes a stop 550, which in this illustrated aspect is angled slightly relative an imaginary line drawn between the pair of distally extending projections 544*a*.

Figure 26:
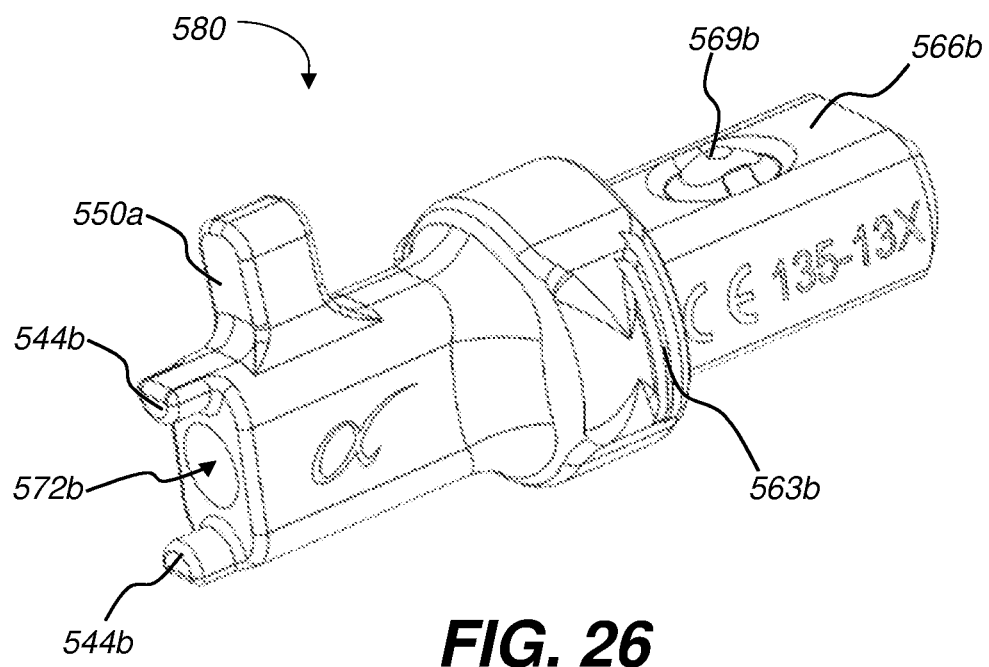
FIG. 26 is a perspective view of another exemplary modular tip to be used with the insertion tool of FIG. 23A.

FIG. 26 illustrates an aspect of another modular tip 580 that, similar to modular tip 580, includes a pair of distally extending projections 544*b*, a pair of gripping surfaces 563*b*, an extension 566*b* with nubs 569*b*, and a lumen 572*b* for receiving engagement rod 547. Modular tip 580 also includes a stop 550*a*, which—similar to stop stop 550 in FIG. 25—is angled slightly relative an imaginary line drawn between the pair of distally extending projections 544*b*. Also, stop 550*a* is positioned slightly proximal to the distal-most surface of modular tip 580.

Figure 27:
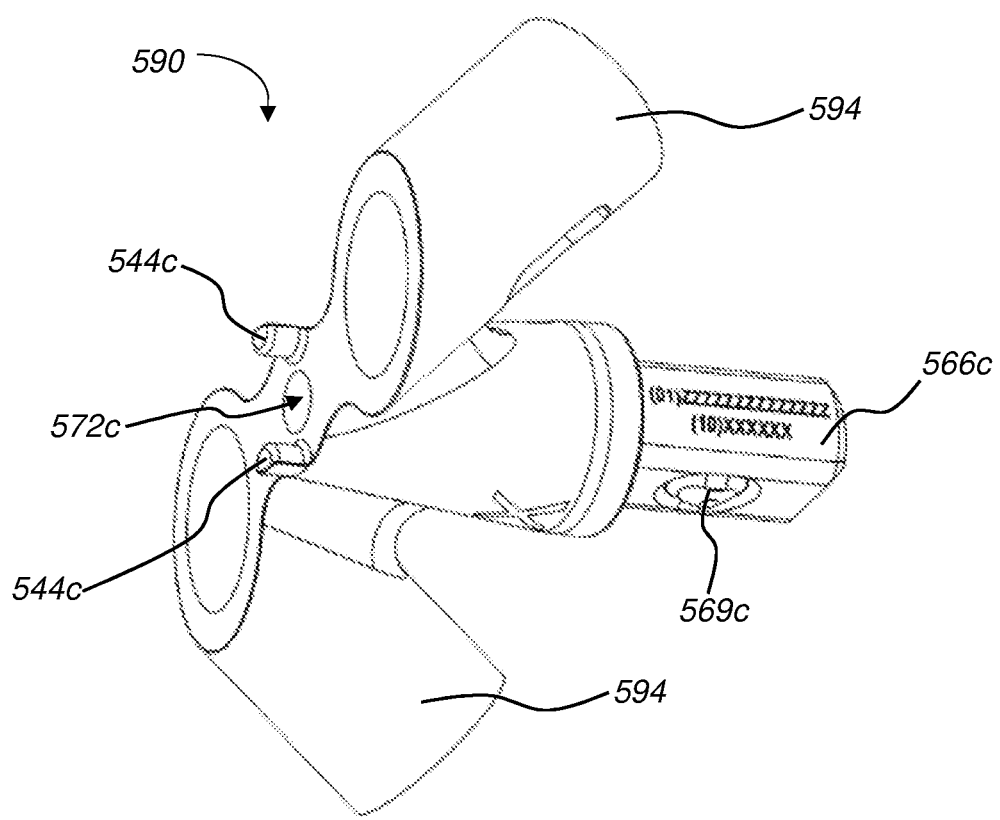
FIG. 27 is a perspective view of another exemplary modular tip to be used with the insertion tool of FIG. 23A.

FIG. 27 illustrates an aspect of another modular tip 590 that, as with the other modular tips, includes distally extending projections 544*c*, an extension 566*c* with nubs 569*c*, and a lumen 572*c* for receiving engagement rod 547. However, modular tip 590 also includes a pair of drill guides 594 configured to align with openings in an implant, such as first and second bores 173, 174 of implant 140. Although modular tip 590 is not illustrated as including a stop like those in the other illustrated modular tips, a skilled artisan will understand that such a feature could be added. A skilled artisan will also understand that the size and shape of drill guides 594 may be adjusted to suit particular implant sizes, screw sizes, implant geometries, etc.

The ability to use a modular tip allows an insertion kit to include one insertion tool with multiple tips rather than multiple insertion tools. Another advantage of modular tips is the ability to adjust and customize particular procedures.

Several aspects are disclosed herein. For example, aspect 1 comprises a method of manufacturing a composite interbody, the method comprising: selecting a metal alloy body having a top surface and an opposing bottom surface; carving out a portion of the top surface of the metal alloy body; carving out a portion of the bottom surface of the metal alloy body; bonding porous metal to the top surface; bonding porous metal to the bottom surface to form a composite metal alloy block; and cutting out a composite interbody from the composite metal alloy block.

Aspect 2 comprises a method of manufacturing a composite interbody, the method comprising: selecting a solid titanium body having a top side and a bottom side; carving out a portion of the top side of the solid titanium body to form a top portion void; carving out a portion of the bottom side of the solid titanium body to form a bottom portion void; diffusion bonding porous titanium to the top portion void; diffusion bonding porous titanium to the bottom portion void, the steps of diffusion bonding porous titanium to the top portion void and bottom portion void forming a composite titanium block; and cutting out a composite interbody from the composite titanium block.

Aspect 3 comprises a method of manufacturing a composite interbody, the method comprising: selecting a solid titanium body having a top surface, an opposing bottom surface, and a side face; bonding porous titanium to the top surface; bonding porous titanium to the bottom surface; bonding a solid titanium block perpendicularly to the side face to form a composite titanium block; and cutting out a composite interbody from the composite titanium block.

Aspect 4 comprises a method of manufacturing a composite interbody, the method comprising: selecting a solid titanium body having a top surface and a bottom surface; carving out a portion of the top surface of the solid titanium body; carving out a portion of the bottom surface of the solid titanium body; bonding metal to the top surface; bonding porous metal to the bottom surface to form a composite titanium body; and cutting out a composite interbody from the composite titanium body.

Aspect 5 comprises a composite interbody system comprising: a body having an anterior face and an opposing posterior face, a top portion and a bottom portion, with a medial portion extending through the body from the anterior face to the opposing posterior face; and the anterior face formed of titanium alloy, the top portion and bottom portion formed of porous titanium, and the medial portion formed of titanium alloy.

Aspect 6 comprises the composite interbody system of Aspect 5, wherein the anterior face and medial portion are formed of a single piece of titanium alloy. Aspect 7 comprises the composite interbody system of aspects 5 or 6, wherein the porous titanium comprises sheets of porous titanium diffusion bonded together to form the porous titanium. Aspect 8 comprises the composite interbody system of any of aspects 5 through 7, wherein the top portion is diffusion bonded to a top surface of the medial portion and the bottom portion is diffusion bonded to a bottom surface of the medial portion.

Aspect 9 comprises a composite interbody system comprising: a body having an anterior face and an opposing posterior face, a top portion and a bottom portion, with a medial portion extending through the body from the anterior face to the opposing posterior face; the anterior face formed of a solid metal alloy, the top portion and bottom portion formed of a porous metal, and the medial portion formed of a solid metal alloy; the anterior face comprising at least one bore for receiving a bone screw; and at least one locking mechanism for preventing back-out of the bone screw.

Aspect 10 comprises the composite interbody of aspect 9, wherein the anterior face further comprises an axial channel proximal to the at least one bore; and wherein the locking mechanism comprises a cylinder with an outwardly projecting tab, the cylinder receivable in the axial channel, and the outwardly projecting tab extending at least partially into the at least one bore.

Aspect 11 comprises the composite interbody of aspect 10, wherein the outwardly projecting tab of the locking mechanism further comprises an angled face to allow the bone screw to deflect the outwardly projecting tab as it is inserted into the at least one bore. Aspect 12 comprises the composite interbody of aspect 10 or 11, wherein the outwardly project tab is biased to extend into the at least one bore after it is deflected by the bone screw.

Aspect 13 comprises the composite interbody of aspect 9, wherein the anterior face further comprises an axial channel proximal to the at least one bore; and wherein the locking mechanism comprises a blocker with at least one outwardly projecting arm, the blocker receivable in the axial channel and rotatable therein between a locked configuration and an open configuration. Aspect 14 includes the composite interbody of any of aspects 9 through 13, wherein the body is cut from the composite metal alloy block formed by the method of aspect 1.

Aspect 15 comprises the composite interbody of any of aspects 9 through 14, wherein the body is cut from the composite titanium block formed by the method of any of aspects 2 through 4. Aspect 16 comprises the composite interbody of any of aspects 9 through 15, wherein the at least one bore is at least partially threaded. Aspect 17 comprises the composite interbody of aspect 16, wherein threads of the at least one bore are configured to engage with corresponding threads on the bone screw. Aspect 18 comprises the composite interbody of aspect 16 or 17, wherein the bone screw has a head portion that is at least partially threaded. Aspect 19 includes the composite interbody of aspect 17 or 18, wherein there is a clearance between the threads of the at least one bore and the corresponding threads on the bone screw.

Aspect 20 comprises a composite interbody system comprising: a body having an anterior face and an opposing posterior face, a top portion and a bottom portion, with a medial portion extending through the body from the anterior face to the opposing posterior face, the medial portion separating the top portion and the bottom portion; the anterior face formed of a solid metal alloy, the top portion and bottom portion formed of a porous metal, and the medial portion formed of a solid metal alloy; the anterior face comprising a first bore for receiving a first bone screw, and a first inwardly extending channel proximal to the first bore, the inwardly extending channel for receiving a first locking mechanism; the anterior face comprising a second bore for receiving a second bone screw, and a second inwardly extending channel proximal to the second bore, the second inwardly extending channel for receiving a second locking mechanism; the first locking mechanism comprising a cylinder receivable into the first inwardly extending channel, the cylinder having an inward end and an outward end, and a first tab projecting outwardly from the outward end of the cylinder, the first tab projecting at least partially into the first bore; and the second locking mechanism comprising a cylinder receivable in the second inwardly extending channel, and a second tab projecting outwardly from the cylinder, the second tab projecting at least partially into the second bore.

Aspect 21 comprises the composite interbody system of aspect 20, wherein the first tab and second tab are biased to project at least partially into the first bore and second bore. Aspect 22 comprises the composite interbody system of aspect 21, wherein the first tab and second tab comprise an angled face. Aspect 23 includes the composite interbody system of aspect 22, wherein the outward end of the cylinder comprises a cut-away to allow the tab of the first locking mechanism to be forced out of the first bore by pressure of an inwardly moving first bone anchor and the tab of the second locking mechanism to be forced out of the second bore by pressure of an inwardly moving second bone anchor. Aspect 24 includes the composite interbody system of aspect 23, wherein the tab of the first locking mechanism and the tab of the second locking mechanism are biased toward projecting at least partially into the first bore and the second bore, respectively.

According to aspect 25, a composite interbody system includes: a body having an anterior face and an opposing posterior face, a top portion and a bottom portion, with a medial portion extending through the body from the anterior face to the opposing posterior face, the medial portion separating the top portion and the bottom portion; the anterior face formed of a solid metal alloy, the top portion and bottom portion formed of a porous metal, and the medial portion formed of a solid metal alloy; the anterior face comprising a first bore for receiving a first bone anchor; the anterior face comprising a second bore for receiving a second bone anchor; and a locking mechanism to prevent back-out of the first bone anchor and the second bone anchor from the first and second bores, respectively.

Aspect 26 includes the composite interbody system of aspect 25, wherein the anterior face further comprises a shaped void for receiving the locking mechanism, the shaped void between the first bore and the second bore; and wherein the locking mechanism comprises a rotatable blocker positioned in the shaped void between the first bore and the second bore, the rotatable blocker having a first, open position wherein bone anchors may be inserted and a second, closed position wherein bone anchors may not be inserted. Aspect 27 comprises the composite interbody system of aspect 26, wherein the rotatable blocker extends into the first bore and the second bore in the second, closed position and wherein the rotatable blocker does not extend into the first bore and the second bore in the first, open position.

Aspect 28 includes the composite interbody system of aspect 27, wherein the body comprises a vertical opening, the locking mechanism further comprises a vertical pin, and wherein the rotatable blocker comprises an aperture for receiving the vertical pin to hold the rotatable blocker in place in the body. Aspect 29 includes the composite interbody system of any of aspects 26 through 28, wherein the rotatable blocker comprises a first outwardly extending arm and a second outwardly extending arm, and wherein the shaped void comprises a first slot for the first outwardly extending arm to rotate within and a second slot for the second outwardly extending arm to rotate within.

Aspect 30 comprises the composite interbody system of aspect 29, wherein the first slot allows the second outwardly extending arm to rotate from about 0 degrees to about 45 degrees and wherein the second slot allows the first outwardly extending arm to rotate from about 180 degrees to about 225 degrees. Aspect 31 includes the composite interbody system of any of aspects 26 through 30, wherein the shaped void further comprises at least one additional cut-out for receiving an insertion tool. Aspect 32 comprises the composite interbody system of any of aspects 26 through 31, wherein the rotatable blocker further comprises threads to mate with an insertion tool.

Aspect 33 includes the composite interbody system of any of aspects 20 through 32, wherein the body is cut from the composite metal alloy block formed by the method of aspect 1. Aspect 34 includes the composite interbody system of any of aspects 20 through 32, wherein the body is cut from the composite titanium block formed by the method of any of aspects 2 through 3. And aspect 35 includes the composite interbody system of any of aspects 20 through 32, wherein the body is cut from the composite titanium body formed by the method of aspect 4.

While the present methods and devices have been specifically described with respect to use in spinal implants, it will be appreciated that other applications are possible and contemplated herein. The various aspects described above, including elements of the various embodiments described above, can be combined to provide further embodiments. Various portions and components of apparatus within the scope of this disclosure, including for example, structural components, can be formed by one or more various suitable manufacturing processes known to those in the art. Similarly, various portions and components of apparatuses within the scope of this disclosure can be made from suitable materials known to those in the art.

The above description has set out various features, functions, methods, and other aspects of the disclosure. Time and further development may change the manner in which the various aspects are implemented. The scope of protection defined by the claims is not intended to be limited to the specific sizes, shapes, features, or other aspects of the disclosed embodiments. The claimed inventions may be implemented or embodied in other forms while still being within the scopes of the concepts disclosed hereby. Also included are equivalents of the elements of the claims that can be made without departing from the scopes of concepts properly protected by the claims that follow.

What is claimed:

1. A composite interbody system comprising:
a body having an anterior face and an opposing posterior face, a top portion and a bottom portion, with a medial portion extending through the body from the anterior face to the opposing posterior face, the medial portion separating the top portion and the bottom portion, the anterior face anterior to the top portion and the bottom portion;
a first locking mechanism and a second locking mechanism;
the anterior face formed of a solid metal alloy, the top portion and bottom portion formed of a porous metal, and the medial portion formed of a solid metal alloy;
the anterior face comprising a first bore for receiving a first bone screw, and a first inwardly extending channel proximal to the first bore, the first inwardly extending channel for receiving the first locking mechanism;
the anterior face comprising a second bore for receiving a second bone screw, and a second inwardly extending channel proximal to the second bore, the second inwardly extending channel for receiving the second locking mechanism;
the first locking mechanism comprising a first cylinder receivable into the first inwardly extending channel, the first cylinder having an inward end and an outward end, and a first tab projecting outwardly from the outward end of the cylinder, the first tab projecting at least partially into the first bore; and
the second locking mechanism comprising a second cylinder receivable in the second inwardly extending channel, the second cylinder having an inward end and an outward end and a second tab projecting outwardly from the cylinder, the second tab projecting at least partially into the second bore,
wherein the first tab and second tab comprise an angled face and are biased to project at least partially into the first bore and second bore, respectively, and
wherein the outward ends of the first and second cylinders each comprise a cut-away to allow, respectively, the first tab of the first locking mechanism to be forced out of the first bore by pressure of an inwardly moving first bone anchor and the second tab of the second locking mechanism to be forced out of the second bore by pressure of an inwardly moving second bone anchor.

2. The composite interbody system of claim 1, wherein the anterior face and the medial portion are formed of a single piece of titanium alloy.

3. The composite interbody system of claim 2, wherein the porous metal comprises sheets of porous titanium diffusion bonded together to form the porous titanium.

4. The composite interbody system of claim 3, wherein the top portion is diffusion bonded to a top surface of the medial portion and the bottom portion is diffusion bonded to a bottom surface of the medial portion.

5. The composite interbody system of claim 1, wherein the body is cut from a composite titanium block formed by a method comprising:
selecting a solid titanium body having a top side and a bottom side;
carving out a portion of the top side of the solid titanium body to form a top portion void;
carving out a portion of the bottom side of the solid titanium body to form a bottom portion void;
diffusion bonding porous titanium to the top portion void;
diffusion bonding porous titanium to the bottom portion void, the steps of diffusion bonding porous titanium to the top portion void and bottom portion void forming a composite titanium block; and
cutting out a composite interbody from the composite titanium block.

6. The composite interbody system of claim 1, wherein the first or the second bore is at least partially threaded.

7. The composite interbody system of claim 6, wherein the threads are configured to engage with corresponding threads on the first or second bone screw, respectively.

8. The composite interbody system of claim 1, wherein the first or second bone screw has a head portion that is at least partially threaded.

* * * * *